(12) United States Patent
Schwartz et al.

(10) Patent No.: US 10,646,896 B2
(45) Date of Patent: May 12, 2020

(54) PATTERNING OF FRAGILE OR NON-PLANAR SURFACES FOR CELL ALIGNMENT

(71) Applicant: THE TRUSTEES OF PRINCETON UNIVERSITY, Princeton, NJ (US)

(72) Inventors: Jeffrey Schwartz, Princeton, NJ (US); Joshua Spechler, Cherry Hill, NJ (US); Romain Fardel, New York, NY (US); Kelly Lim, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 115 days.

(21) Appl. No.: 15/649,033

(22) Filed: Jul. 13, 2017

(65) Prior Publication Data

US 2017/0312780 A1  Nov. 2, 2017

Related U.S. Application Data

(63) Continuation-in-part of application No. PCT/US2016/012791, filed on Jan. 11, 2016.

(60) Provisional application No. 62/152,222, filed on Apr. 24, 2015, provisional application No. 62/105,804, filed on Jan. 21, 2015.

(51) Int. Cl.
 *B32B 3/10* (2006.01)
 *B05D 1/32* (2006.01)
 *G03F 7/00* (2006.01)

(52) U.S. Cl.
 CPC ............. *B05D 1/32* (2013.01); *G03F 7/0002* (2013.01); *C12N 2533/32* (2013.01); *C12N 2535/10* (2013.01)

(58) Field of Classification Search
 None
 See application file for complete search history.

(56) References Cited

U.S. PATENT DOCUMENTS

| | | |
|---|---|---|
| 6,645,644 B1 | 11/2003 | Schwartz et al. |
| 7,396,594 B2 | 7/2008 | Schwartz et al. |
| 7,879,456 B2 | 2/2011 | Schwartz et al. |
| 9,056,154 B2 | 6/2015 | Schwartz et al. |
| 2002/0050220 A1 | 5/2002 | Schueller et al. |
| 2002/0095219 A1 | 7/2002 | Nelles et al. |
| 2004/0096476 A1 | 5/2004 | Uhrich et al. |

(Continued)

OTHER PUBLICATIONS

Pae et al., "Attachment and growth behaviour of human gingival fibroblasts on titanium and zirconia ceramic surcases," Biomed. Mater. (2009)4:1-7.

(Continued)

*Primary Examiner* — Christopher M Polley
(74) *Attorney, Agent, or Firm* — Fox Rothschild LLP

(57) ABSTRACT

A construct that supports cell attachment and alignment including a substrate that is incompatible with photolithography conditions, containing a physical pattern in at least part of one surface, the physical pattern optionally bearing a coating of a metal alkoxide, oxide or mixed oxide-alkoxide thereon and a Self-Assembled Monolayer of Phosphonate (SAMP) covalently attached thereto, which phosphonate contains functionality adapted for cell binding. The construct optionally also contains cells attached thereto. Also disclosed are methods of preparing such a construct.

37 Claims, 23 Drawing Sheets

(56) References Cited

U.S. PATENT DOCUMENTS

| | | | |
|---|---|---|---|
| 2006/0085063 A1* | 4/2006 | Shastri | A61F 2/02 623/1.41 |
| 2006/0194008 A1* | 8/2006 | Schwartz | A61L 27/32 428/34.4 |
| 2008/0131709 A1 | 6/2008 | Hanson et al. | |
| 2008/0299169 A1 | 12/2008 | Hoffman-Kim et al. | |
| 2009/0104474 A1 | 4/2009 | Schwartz et al. | |
| 2014/0330392 A1 | 11/2014 | Schwartz et al. | |

OTHER PUBLICATIONS

Chang et al., "Modulation of neural network activity by patterning," Biosensors & Bioelectronics (2001); 16:527-533.

Viviani, Barbara, "Preparation and Coculture of Neurons and Glial Cells," Current Protocols in Cell Biology (2006); 32:2.7.1-2.7.21.

Saneinejad et al., "Patterned glass surfaces direct cell adhesion and process outgrowth of primary neurons of the central nervous system," Biomed. Mater. Res. (1998); 42(10):13-19.

Teixeira et al., "Responses of human keratocytes to micro- and nanostructured substrates" J. Biomed. Mater. Res. (2004); 71A:369-376.

Danahy et al., "Self-assembled Monolayrs of a,w-Diphosphonic Acids on Ti Enable Complete or Spatially Controlled Surface Derivatization," Langmuir (2004); 20:5333-5337.

* cited by examiner

| Spectrum | In stats. | C | O | Zr | Total |
|---|---|---|---|---|---|
| Spectrum 1 | Yes | 52.89 | 29.83 | 17.28 | 100.00 |
| Spectrum 2 | Yes | 63.48 | 30.75 | 5.77 | 100.00 |
| Spectrum 3 | Yes | 53.22 | 30.91 | 15.88 | 100.00 |
| Spectrum 4 | Yes | 65.30 | 29.38 | 5.32 | 100.00 |
| Spectrum 5 | Yes | 53.70 | 31.39 | 14.90 | 100.00 |
| Mean | | 57.72 | 30.45 | 11.83 | 100.00 |
| Std. deviation | | 6.13 | 0.82 | 5.80 | |

Electron Image 1

Zr La1

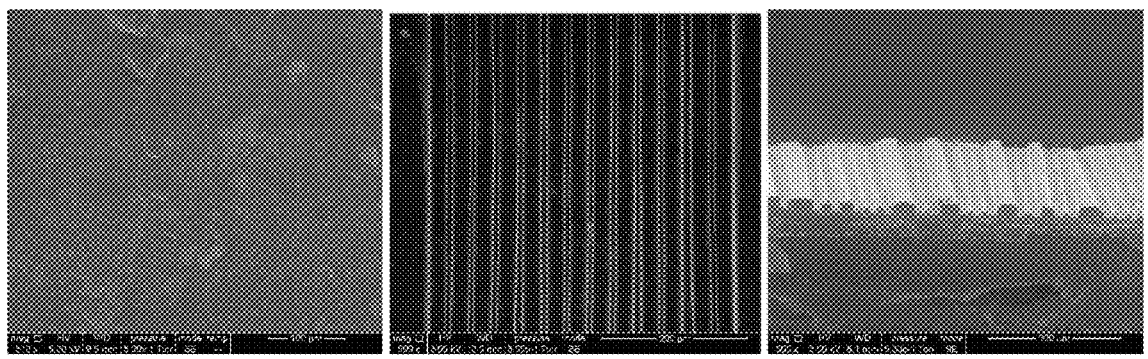
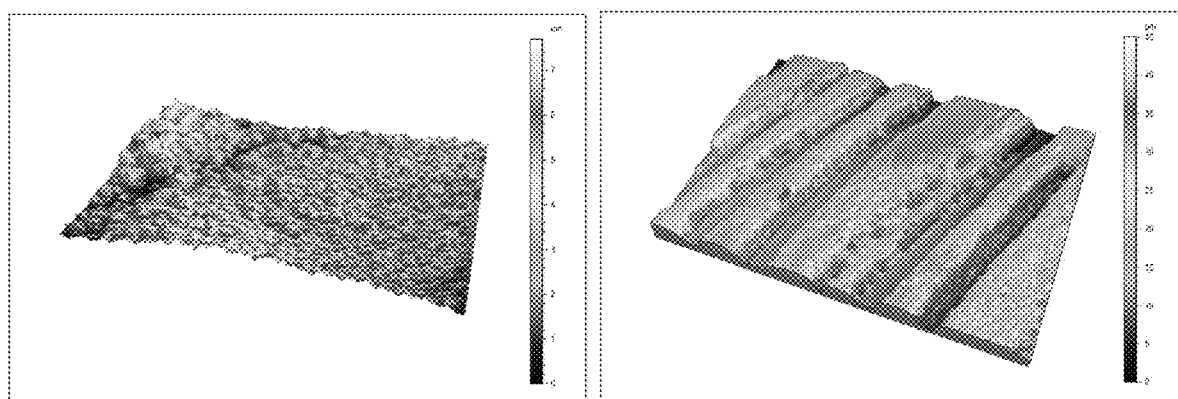
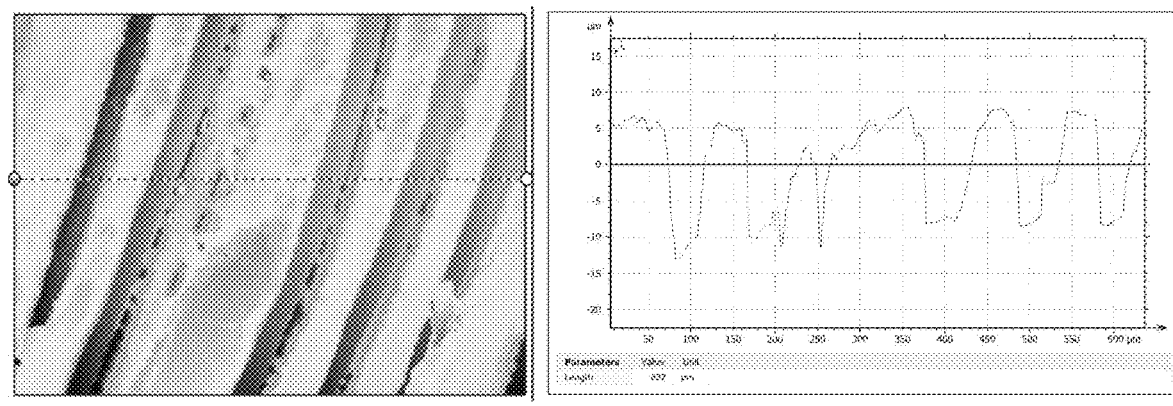
FIGs. 19A, 19B, 19C, 19D, 19E, 19F and 19G

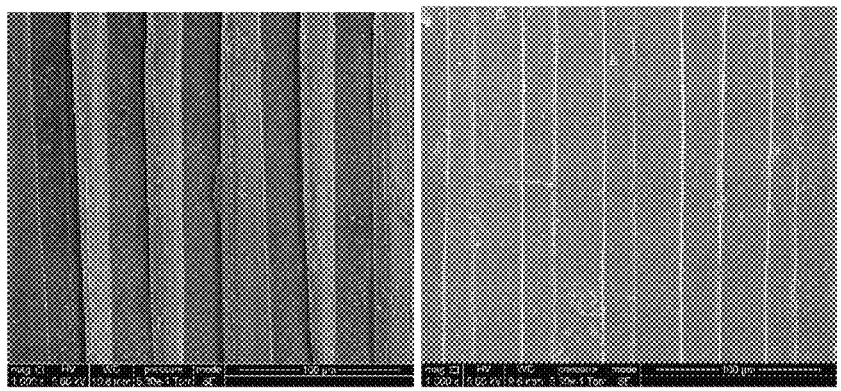
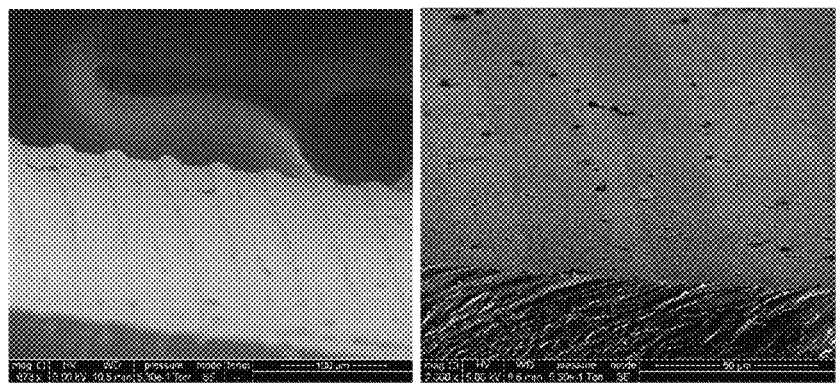
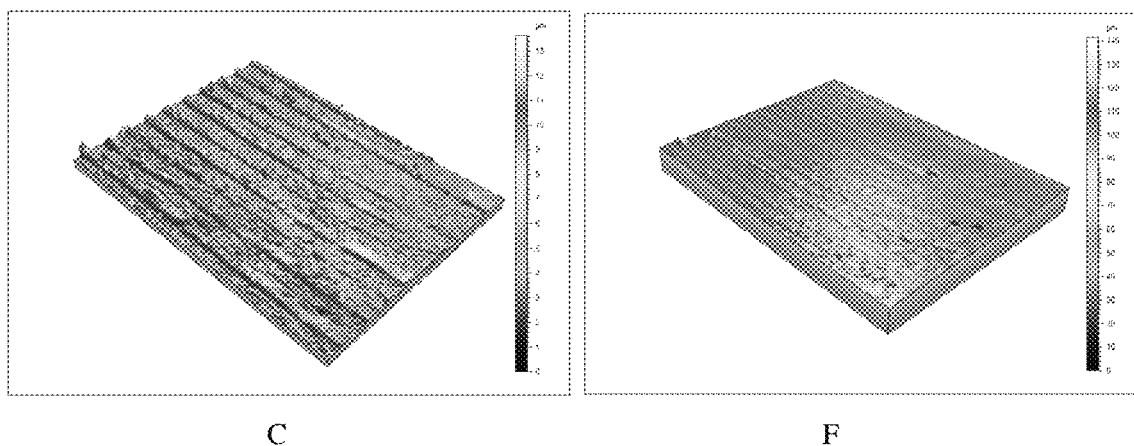
FIGs. 21A, 21B, 21C, 21D, 21E and 21F

A

B

PATTERNING OF FRAGILE OR NON-PLANAR SURFACES FOR CELL ALIGNMENT

CROSS-REFERENCE TO RELATED APPLICATIONS

This application is a continuation-in-part of PCT Application No. PCT/US2016/012791, filed on Jan. 11, 2016, which claims the benefit of priority of U.S. Provisional Applications No. 62/105,804, filed on Jan. 21, 2015, and 62/152,222, filed on Apr. 24, 2015. The entire disclosures of all of these applications are incorporated herein by reference.

STATEMENT REGARDING FEDERALLY SPONSORED RESEARCH OR DEVELOPMENT

This invention was made with government support under Grant No. DMR-0819860 and No. DMR-1420541 awarded by the National Science Foundation. The government has certain rights in the invention.

FIELD OF THE DISCLOSED SUBJECT MATTER

The presently disclosed subject matter relates to scaffolds or constructs useful for directed cellular growth where the scaffolds comprise patterned fragile or non-planar (curved) surfaces. Such scaffolds are useful as templates for nerve regeneration, muscle growth, and other in vitro and in vivo tissue applications.

BACKGROUND

Central and peripheral nerve injury results in immediate inflammation and scar tissue formation that obstructs natural and surgical healing. To regenerate a severed neural connection, an ideal scaffold would serve as a bridge to guide neural cell navigation to traverse the injury site. Available, clinically approved conduits for nerve guidance, also referred to as "nerve guides", may be limited by inadequate waste exchange and inadequate diffusion of nutrients and oxygen, compression of the regenerating nerve, and a lack sufficient extracellular matrix (ECM) to guide neurons. A crucial step in natural nerve development in both the peripheral and central nervous systems involves formation of an ECM bridge to guide glial cells that support migrating neural cells; ECM is particularly effective for guidance of nerve development because it provides biochemical cues, including neurotrophic factors, and structural information, in the form of highly aligned ECM fibrils that are essential for inducing and directing axonal outgrowth.

There is a continuing need for new and improved scaffolds that will support nerve regeneration, muscle growth, and other in vitro and in vivo tissue applications. The polymers used for such scaffolds must be biocompatible and/or biodegradable, and must have physical properties appropriate to the specific application. For nerve regeneration conduits, or nerve guides, such polymers must have appropriate flexibility to be rolled or cast into microtubes, and must be compatible with in vivo insertion or implantation.

SUMMARY OF THE DISCLOSED SUBJECT MATTER

The patterned or textured polymer substrates of the present disclosure provide such desirable scaffolds.

One aspect of the invention is directed to a polymeric substrate that is incompatible with photolithography conditions, at least a portion of a surface of which comprises a material suitable for cell attachment, in a pattern which is raised above the surface of the substrate. In one embodiment of the polymeric substrate the raised pattern comprises the polymer of the polymeric substrate. In another embodiment of the polymeric substrate the raised pattern comprises at least one cell-binding or cell-adhesive material. The polymeric substrate can be incompatible with photolithography conditions due to one or more incompatibilities selected from temperature incompatibility, solvent incompatibility, reagent incompatibility, and surface geometry incompatibility. In one embodiment the surface geometry incompatibility comprises surface curvature. In some embodiments the curvature comprises a curved surface selected from the group consisting of inward-curving concave surfaces and outward-curving convex surfaces.

In one embodiment the polymeric substrate is in the form of a tube or a tube-like structure and the raised-patterned surface is on the interior of the tube or tube-like structure. The tube or tube-like structure can be a rolled species, a rolled-up system, a preformed tube, or a species of similar geometry.

Another aspect of the invention is directed to a method of patterning a surface of a polymeric substrate which is incompatible with photolithography conditions, comprising the steps of a) providing a shadow mask, b) applying the shadow mask to a surface of the polymeric substrate to form a masked substrate, c) applying pressure to the shadow mask surface of the masked substrate, optionally with heating sufficient to form a phase transition in the polymer of the polymeric substrate, d) optionally, cooling the masked substrate, and e) removing the mask to reveal a patterned polymeric surface. The polymeric substrate can be incompatible with photolithography conditions due to one or more incompatibilities selected from the group consisting of temperature incompatibility, solvent incompatibility, reagent incompatibility, and surface geometry incompatibility. In some embodiments the surface geometry incompatibility comprises surface curvature. In some embodiments the patterning is on the inside surface of a tube, a tube-like substrate, or a folded substrate. The tube or tube-like substrate can comprise a rolled species, a rolled-up system, a preformed tube, or a species of similar geometry. In one embodiment the polymeric substrate is a preformed tube having patterning on the inside surface.

Yet another aspect of the invention is directed to a method of preparing a shadow mask for patterning the inside surface of a polymeric tube which is incompatible with photolithography conditions, comprising the steps of a) providing a coupon of polymer having a thickness of about 10 μm to about 120 μm, and having appropriate dimensions to completely cover the inside surface of a polymeric tube, and b) ablating the coupon to remove selected segments of the polymer, providing a desired pattern; wherein the coupon polymer is adherent to the interior surface of the polymeric tube such that the peel strength therebetween is less than the tensile strength of either of the coupon polymer or the polymeric tube. In one embodiment of the method the ablation comprises laser ablation. The polymeric tube can be incompatible with photolithography conditions due to one or more incompatibilities selected from the group consisting of temperature incompatibility, solvent incompatibility, reagent incompatibility, and surface geometry incompatibility. In one embodiment the surface geometry incompatibility comprises surface curvature.

Still another aspect of the invention is directed to a construct which supports cell attachment and alignment, comprising a) a substrate which is incompatible with photolithography conditions; b) a patterned coating of a metal alkoxide, oxide or mixed oxide-alkoxide disposed thereon; and c) a phosphonic acid covalently attached to b), which phosphonic acid contains functionality adapted for cell binding. In one embodiment the metal alkoxide is selected from Zr, Ti, Group 5 or Group 6 metals. In one embodiment the metal alkoxide is a zirconium alkoxide. One embodiment of the construct further comprises cells attached thereto. Another embodiment of the construct further comprises an aligned extracellular matrix (ECM). The substrate can be incompatible with photolithography conditions due to one or more incompatibilities selected from the group consisting of temperature incompatibility, solvent incompatibility, reagent incompatibility, and surface geometry incompatibility. In one embodiment the surface geometry incompatibility comprises surface curvature.

In some embodiments of the construct, the phosphonic acid comprises one or more functional groups selected from the group consisting of polyol moieties, sugar alcohol moieties, hydroxyl functional groups, amino functional groups, carboxylic acid functional groups, carboxylate ester functional groups, phosphonic acid functional groups, phosphonate functional groups, ether functional groups, alkyne functional groups, azide functional groups and thiol functional groups. In one embodiment the phosphonic acid is 1,4-butanediphosphonic acid. In some embodiments of the construct the substrate comprises a polymer selected from the group consisting of polyamides, polyurethanes, polyureas, polyesters, polyketones, polyimides, polysulfides, polysulfoxides, polysulfones, polythiophenes, polypyridines, polypyrroles, polyethers, silicone (polysiloxanes), polysaccharides, fluoro-polymers, epoxies, aramides, amides, imides, polypeptides, polyolefins, polyethylene, polystyrene, polypropylene, liquid crystal polymers, thermoplastics, polyvinyls, poly(vinyl alcohol), polyacrylics, polyacrylates, poly(acrylic acid), polycarbonates, polytetrafluoroethylene (PTFE), polyethylene terephthalate (PET), poly(vinyl-pyrrolidone), poly(-hydroxyethyl methacrylate), poly(N-vinylpyrrolidone), poly(methyl methacrylate), polyethylene-co-vinyl acetate), poly(methacrylic acid), polylactides (PLA), polyglycolides (PGA), poly(lactide-co-glycolides) (PLGA), polylactones, polyanhydrides, polyphosphazenes, polyorthoesters, polycaprolactone fumarate (PCLF), oligo-(polyethylene glycol) fumarate (OPF), PEDOT:PSS, poly(ethylene oxide), poly(ethylene glycol), cross-linked poly(acrylic acid), poly(acrylamides), aliphatic polyether-based thermoplastic polyurethanes, sucrose, carbohydrate glass, biopolymers such as silk, collagen, alginate, chitosan, and chondroitin, copolymers and derivatives thereof, and composites including these polymers. In preferred embodiments the substrate polymer comprises PCLF, OPF or an aliphatic polyether-based thermoplastic polyurethane. In a preferred embodiment the substrate polymer is PCLF. In another preferred embodiment the substrate polymer is OPF. In a further preferred embodiment, the substrate polymer is an aliphatic polyether-based thermoplastic polyurethane. The aliphatic polyether-based thermoplastic polyurethane can be TECOFLEX™ EG-80A.

In one embodiment of the construct, the patterned coating is on the inside surface of a tube, a tube-like substrate, or a folded substrate. The tube or tube-like substrate can comprise a rolled species, a rolled-up system, a preformed tube, or a species of similar geometry.

Another aspect of the invention is directed to a method of preparing a construct which supports cell attachment and alignment, the method comprising a) providing a substrate which is incompatible with photolithography conditions; b) preparing a shadow mask template consisting of a material which is adherent to the substrate such that the peel strength is less than the tensile strength of the shadow mask and substrate material; and c) adhering the shadow mask template to the substrate to form a substrate-mask ensemble. One embodiment of the method further comprises d) exposing the substrate-mask ensemble to a metal alkoxide to form a treated substrate-mask ensemble; e) warming the treated ensemble and removing the mask from the treated substrate-mask ensemble to form a metal oxide/alkoxide patterned surface; and f) covalently attaching to the patterned surface a phosphonic acid containing functionality adapted for cell binding, to form the construct. In one embodiment the metal alkoxide is selected from Zr, Ti, Group 5 or Group 6 metals. In one embodiment the metal alkoxide is a zirconium alkoxide. Another embodiment of the method further comprises d) exposing the substrate-mask ensemble to a cell-adhesive biomaterial to form a treated substrate-mask ensemble; and e) removing the mask from the treated substrate-mask ensemble to form a cell-adhesive patterned surface to form the construct. Other embodiments further comprise the step of attaching cells to the construct. Still other embodiments further comprise the step of incubating the construct to form an aligned extracellular matrix (ECM). The substrate can be incompatible with photolithography conditions due to one or more incompatibilities selected from the group consisting of temperature incompatibility, solvent incompatibility, reagent incompatibility, and surface geometry incompatibility. In one embodiment the surface geometry incompatibility comprises surface curvature. In some embodiment of the method the substrate comprises a tube, a tube-like, or a folded structure and wherein the inside surface of the substrate is patterned. The tube or tube-like structure can comprise a rolled species, a rolled-up system, a preformed tube, or a structure of similar geometry.

In some embodiments of the method the phosphonic acid comprises one or more functional groups selected from polyol moieties, sugar alcohol moieties, hydroxyl functional groups, amino functional groups, carboxylic acid functional groups, carboxylate ester functional groups, phosphonic acid functional groups, phosphonate functional groups, ether functional groups, alkyne functional groups, azide functional groups and thiol functional groups. In one preferred embodiment the phosphonic acid is 1,4-butanediphosphonic acid.

In some embodiments of the method the substrate comprises a polymer selected from the group consisting of polyamides, polyurethanes, polyureas, polyesters, polyketones, polyimides, polysulfides, polysulfoxides, polysulfones, polythiophenes, polypyridines, polypyrroles, polyethers, silicone (polysiloxanes), polysaccharides, fluoro-polymers, epoxies, aramides, amides, imides, polypeptides, polyolefins, polyethylene, polystyrene, poly-propylene, liquid crystal polymers, thermoplastics, polyvinyls, poly(vinyl alcohol), polyacrylics, polyacrylates, poly(acrylic acid), polycarbonates, polytetrafluoroethylene (PTFE), polyethylene terephthalate (PET), poly(vinyl-pyrrolidone), poly(-hydroxyethyl methacrylate), poly(N-vinylpyrrolidone), poly(methyl methacrylate), polyethylene-co-vinyl acetate), poly(methacrylic acid), polylactides (PLA), polyglycolides (PGA), poly(lactide-co-glycolides) (PLGA), polylactones, polyanhydrides, polyphosphazenes, polyorthoesters, polycaprolactone fumarate (PCLF), oligo- (polyethylene glycol) fumarate (OPF), PEDOT:PSS, poly (ethylene oxide), poly(ethylene glycol), cross-linked poly (acrylic acid), poly(acrylamides), aliphatic polyether-based thermoplastic polyurethanes, sucrose, carbohydrate glass, biopolymers such as silk, collagen, alginate, chitosan, and chondroitin, copolymers and derivatives thereof, and composites including these polymers. In one preferred embodiment the substrate polymer comprises PCLF, OPF or an aliphatic polyether-based thermoplastic polyurethane. In a particularly preferred embodiment the substrate polymer is PCLF, or OPF, or an aliphatic polyether-based thermoplastic polyurethane. The aliphatic polyether-based thermoplastic polyurethane can be TECOFLEX™ EG-80A.

BRIEF DESCRIPTION OF THE DRAWINGS

FIGS. 10-16 are scanning electron micrographs (SEMs) of the inside of a 1.5 mm ID PCLF tube. The tube, with the shadow mask inserted, is exposed to vapor of zirconium tetra(tert-butoxide), Zr(O-tBu)$_4$, for either 10 min or 5 min, as noted, then warmed, followed by treatment with a solution of 1,4-diphosphonobutane.

FIG. 10A shows a SEM of the inside of a 1.5 mm ID PCLF tube, 10-min Zr tetra(tert-butoxide) exposure, scale bar is 3 mm (50× magnification). There is some waviness in the pattern because of the fragility of the mask. FIG. 10B shows a 200× magnification in the region of the "structural bar" of the mask; scale bar is 500 μm.

FIG. 11A shows a SEM of the inside of a 1.5 mm ID PCLF tube, 5-min Zr tetra(tert-butoxide) exposure, 100× magnification. FIG. 11B shows a 200× magnification in the region of the structural bar.

FIG. 12A shows a SEM of the inside of a 1.5 mm ID PCLF tube, 5-min Zr tetra(tert-butoxide) exposure, 1000× magnification. FIG. 12B shows a 1500× magnification.

FIG. 13 shows a SEM of the inside of a 1.5 mm ID PCLF tube, 5-min Zr tetra(tert-butoxide) exposure, 1500× magnification showing Zr concentrated in alternating stripes, as expected based on the masking pattern. Apparently a small amount of Zr has crept under the mask.

FIG. 14A shows a SEM of the inside of a 1.5 mm ID PCLF tube, 5-min Zr tetra(tert-butoxide) exposure, 1500× magnification. FIG. 14B shows an XPS analysis of the same tube, indicating that Zr is concentrated in the desired stripe motif.

FIG. 15 shows a SEM of the inside of a 1.5 mm ID PCLF tube, 5-min Zr tetra(tert-butoxide) exposure, 75× magnification in segments 1 through 3 of 5 of the tube.

FIG. 16 shows a SEM of the inside of the same 1.5 mm ID PCLF tube, 5-min Zr tetra(tert-butoxide) exposure, 75× magnification in segments 4 and 5 of 5 of the tube.

FIGS. 19A, 19B, 19C, 19D, 19E, 19F and 19G show the results of embossing OPF with a shadow mask: Un-embossed OPF (19A), and top view (19B) and cross section (19C) of an embossed OPF sample observed under environmental scanning electron microscopy (ESEM) in low vacuum mode. A 3D confocal microscopy of a piece of dehydrated OPF at room temperature and pressure before and after embossing are shown in 19D and 19E, respectively. A 3D confocal image and its profile at the drawn line are shown in 19F and 19G, respectively. Embossing changes the physical appearance of the OPF, forming ridges ranging from 10 μm to 20 μm in height.

FIGS. 21A, 21B, 21C, 21D, 21E and 21F show the results of embossing TECOFLEX™ EG-80A: Embossing with physical modifications under ESEM for top view (21A) and cross section (21B), and 3D confocal microscopy (21C). Embossing without physical modifications under ESEM for top view (21D) and cross section (21E), and 3D confocal microscopy (21F). The elasticity of TECOFLEX™ limited physical modifications on its surface, but the shadow mask was still adhered in both cases. Only the edges of the pattern underwent physical modifications.

DETAILED DESCRIPTION OF PREFERRED EMBODIMENTS

Figure 1:
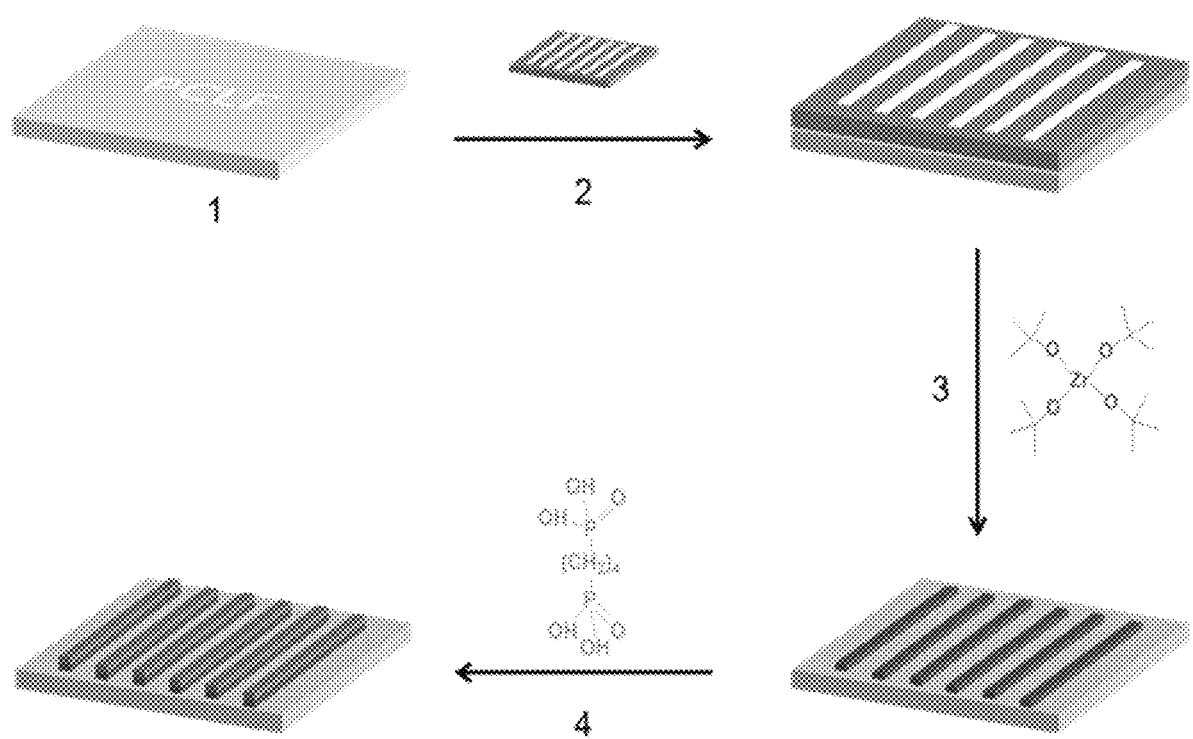
FIG. 1 shows a schematic representation for surface patterning a fragile or non-planar polymer such as PCLF.

Photolithography is a common chemical treatment carried out to pattern thin films or bulk substrates. Using a suitable photoresist deposited onto the substrate and a photomask, the layer of photoresist is treated with UV light to transfer a geometric pattern from the mask to the material below the photoresist. For positive photoresist, the unexposed regions will remain covered by photoresist and the regions not covered by the photomask will be washed away by subsequent chemical treatments, leaving behind patterns on the treated substrate. Despite being a simple process, certain materials are incompatible with this microfabrication process. For example, a previous attempt to pattern polycaprolactone fumarate (PCLF) by photolithography showed that the photoresist used in this process could not be washed off at the end of the light treatment, thereby destroying the inherent material instead of patterning it. Photolithography is also incompatible with non-flat surfaces. Therefore, as opposed to a chemical mask, a physical alternative which incorporates shadow masking was utilized.

Shadow masking is a process whereby a physical mask is used to shadow surface areas of materials that will not be treated. Thus, for shadow masking to successfully pattern the surface of a material, an intimate contact between the mask and the material must be established. Shadow masking has been successfully carried out by the present inventors with soft polymers that have fairly low glass transition temperatures ($T_g$). The relatively low $T_g$ can be easily reached by gentle heating over a hotplate, at which point the materials become soft and sticky, and can be readily adhered onto a shadow mask. It has now been discovered that the shadow masks can be pressed onto the material, e.g., between two clean glass slides, and then removed after surface treatments, leaving behind patterned surface treatments on areas that were not physically covered by the shadow mask. These shadow masks can be cleaned and reused. In this way such masks are used as a mechanical contrivance, like a die, to physically emboss the surface of suitable substrate polymers.

Suitable substrate polymers have a relatively low glass transition temperature ($T_g$), between about 50 and about 100° C., preferably about 55 to about 90° C. Such polymers can be selected from the group consisting of polyamides, polyurethanes, polyureas, polyesters, polyketones, polyimides, polysulfides, polysulfoxides, polysulfones, polythiophenes, polypyridines, polypyrroles, polyethers, silicone (polysiloxanes), polysaccharides, fluoro-polymers, epoxies, aramides, amides, imides, polypeptides, polyolefins, polyethylene, polystyrene, poly-propylene, liquid crystal polymers, thermoplastics, polyvinyls, poly(vinyl alcohol), polyacrylics, polyacrylates, poly(acrylic acid), polycarbonates, polytetrafluoroethylene (PTFE), polyethylene terephthalate (PET), poly(vinyl-pyrrolidone), poly(-hydroxyethyl methacrylate), poly(N-vinylpyrrolidone), poly(methyl methacrylate), polyethylene-co-vinyl acetate), poly(methacrylic acid), polylactides (PLA), polyglycolides (PGA), poly(lactide-co-glycolides) (PLGA), polylactones, polyanhydrides, polyphosphazenes, polyorthoesters, polycaprolactone fumarate (PCLF), oligo-(polyethylene glycol) fumarate (OPF), PEDOT:PSS, poly(ethylene oxide), poly(ethylene glycol), cross-linked poly(acrylic acid), poly(acrylamides), aliphatic polyether-based thermoplastic polyurethanes, sucrose, carbohydrate glass, biopolymers such as silk, collagen, alginate, chitosan, and chondroitin, copolymers and derivatives thereof, and composites including these polymers. Preferably the polymer is selected from the group consisting of polycaprolactone fumarate (PCLF), oligo-(polyethylene glycol) fumarate (OPF), and aliphatic polyether-based thermoplastic polyurethanes (such as TECOFLEX™ polymers, e.g. TECOFLEX™ EG-80A). In one preferred embodiment the substrate polymer is PCLF. Another preferred embodiment of the substrate polymer is OPF. Another preferred embodiment is an aliphatic polyether-based thermoplastic polyurethane, such as TECOFLEX™ EG-80A.

Representatives of the aliphatic polyether-based thermoplastic polyurethane class include the commercial offerings of Lubrizol under the tradename TECOFLEX™. These polymers are the reaction products of dodecahydro-methylene diphenyl diisocyanate ($H_{12}$-MDI, also known as 4,4'-dicyclohexylmethane diisocyanate) and α,ω-diols (such as polytetramethylene glycol and 1,4-butanediol), as represented by the following reaction scheme:

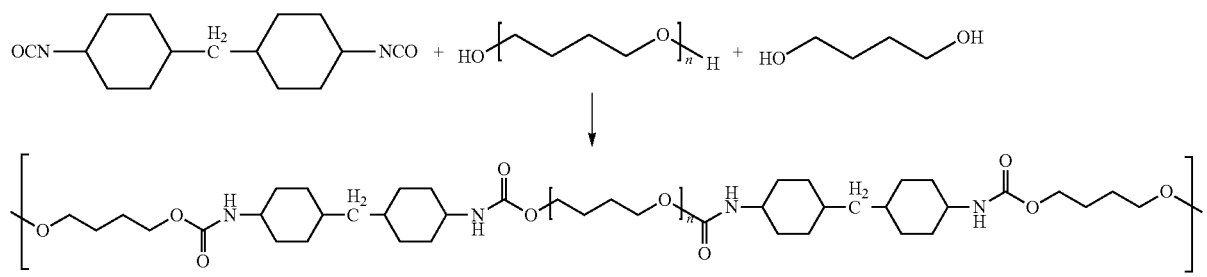

Suitable commercial TECOFLEX™ polymer grades include EG-80A, EG-85A, EG-93A, EG-100A, EG-60D, EG-65D, EG-68D, and EG-72D.

Suitable shadow mask polymers include, without limitation, polyimides, poly(methylmethacrylate) (PMMA) and parylenes. Parylenes include, without limitation, parylene N, parylene C and parylene D. Preferably the parylene is parylene C. The shadow masks are preferably made of KAPTON®, a flexible polyimide film that remains stable throughout a wide range of temperatures (−269° C. to 400° C.). The patterns used were stripes with a pitch of 50 μm and 15 μm wide lines surrounded by about 35 μm of KAPTON® or other polymer. The resulting patterns that were developed from these masks were approximately 30 μm alternating stripes.

Shadow masks are preferably formed by ablating appropriate polymer coupons. Preferably the ablation is laser ablation; therefore, the masking polymers should be sensitive to laser ablation. Masks should be thick enough to produce a useful embossed pattern, but not so thin that the mask will fracture. Also the shadow masks should have an appropriate balance of rigidity and flexibility. If the shadow mask is too thick, it will not conform to the substrate polymer, especially for a 3D substrate. Typically shadow masks for embossing have a thickness of about 25 µm. In some embodiments the embossing shadow masks are about 20 to about 30 µm thick. The masks can be 20, or 21, or 22, or 23, or 24, or 25, or 26, or 27, or 28, or 29, or 30 µm thick. For the reasons discussed above, the mask polymers themselves should also have an appropriate balance of rigidity and flexibility. Further, if the embossing mask polymer is too adhesive (sticky or "wet"), the mask might not be able to be removed once the embossing takes place.

According to one embodiment, a device for nerve regeneration is provided, including a scaffold polymer supporting a native, highly aligned ECM template to stimulate and guide neurite outgrowth across an injury site. The complexity of a native ECM characterized by highly aligned fibrils renders it virtually impossible to synthesize de novo in the lab. However, rather than attempting to fabricate a synthetic matrix scaffold, the present invention recapitulates the inherent complexity of ECM by inducing cells to construct it.

The present invention demonstrates that development of a chemically patterned polymer substrate provides a surface that facilitates the construction of a highly aligned native-like ECM by fibroblast cells plated on the surface. To demonstrate the utility of this cell-assembled ECM to direct neurite outgrowth, neural analog PC12 cells were plated on a decellularized ECM that was assembled by fibroblast cells on a 1,4-butanediphosphonic acid-functionalized surface. Unpatterned substrates induce the formation of ECM marked by fibronectin fibrils in random orientation (unpatterned ECM); this unpatterned ECM directs neurite outgrowth by PC12 cells, but randomly, not directionally. A patterned ECM, constructed by fibroblasts plated on 10×10 1,4-butanediphosphonic acid-patterned PET (poly(ethylene terephthalate)) or PCLF (polycaprolactone fumarate), however, directs neurite outgrowth in register with the aligned ECM and underlying chemical pattern.

That neuron surrogate cells plated on a decellularized, highly aligned ECM platform extend neurites in the direction of the ECM fibrils indicates that a cell-assembled matrix provides a starting point for constructing a nerve regeneration scaffold. A device employing PET as a scaffold polymer, however, would not be useful for addressing nerve regeneration because of a mechanical properties mismatch: The elastic modulus of PET (2 GPa) is 6 orders of magnitude stiffer than the glial cells that support neurons and 5 orders of magnitude stiffer than the fibroblasts that assemble the ECM. To support an ECM template that could be used to effect nerve regeneration in vivo, a scaffold polymer with the correct mechanical properties should be employed.

As disclosed in international patent publication WO 2012/138732, polycaprolactone fumarate (PCLF) is a polymer developed by neurosurgeons at the Mayo Clinic for repair of the peripheral nervous system (PNS); unlike the polymers PET, PEEK, and nylon, PCLF has been formulated to match the mechanical properties of a peripheral nerve. Conduits fabricated from PCLF have been shown to be biocompatible when used to repair a sciatic nerve defect in a rat model. While PCLF conduits are biocompatible and mechanically suited for the PNS, such conduits alone do not stimulate and guide individual axons that must bridge the gap between the two ends of a severed nerve; further, their closed structure may inhibit waste removal and the diffusion of nutrients and oxygen to the regenerating nerve.

Nerve conduits, such as PCLF tubes, used in vivo are of different sizes with respect to their internal diameter (ID), depending on the size of the neurons, which is also related to species. Thus, for rat model testing, smaller ID tubes are required, in the range of about 1 to about 1.5 mm ID. However, for human use the conduits should be about 5 to about 8 mm ID. The presently disclosed patterning method allows the construction of nerve conduits having a broad range of internal diameters, from about 1 mm to about 8 mm, and beyond.

By providing spatially organized, cell-assembled ECM as a guidance platform, the translation of directed neurite outgrowth from the initially tested model polymer PET to an open PCLF polymer substrate, enhances the utility of PCLF as a nerve regeneration scaffold. In one specific embodiment the nerve regeneration scaffold or construct is in the form of a tube or tube-like structure, or a folded device. The tube or tube-like structure can be a rolled species, a rolled-up system, a preformed tube, or a species of similar geometry.

Fundamentally, a patterned interface is essential to the assembly of the highly aligned, native-like ECM by fibroblast cells plated on PET; a striped chemical pattern of 1,4-butanediphosphonic acid templates the adhesion, spreading and proliferating the cells in alignment and facilitating their construction as a similarly aligned matrix. Alternatively, a physically patterned interface in the polymer itself may be sufficient to induce the assembly of a highly aligned ECM, vide infra. The method for chemically functionalizing PET with a patterned $ZrO_2$/SAMP (Self-Assembled Monolayer of Phosphonate) interface involves photolithographic patterning of PET substrates followed by vapor deposition of a volatile organometallic complex to link the cell adhesive phosphonate to the polymer in a striped pattern. This process proved to be incompatible with PCLF because of the adhesion between the photolithographic reagents and PCLF. Due to the incompatibility of the photolithographic process and the polymer, in order to achieve patterning of PCLF with 1,4-butanediphosphonic acid a new process had to be developed based on physical masking for chemical evaporation rather than photolithographic masking.

While PCLF's unique properties make it ideally suited for peripheral nerve repair, its surface chemistry renders it especially problematic for photolithography. Substrates patterned by photolithography are generally pre-baked (e.g., at 95° C.); however, upon heating PCLF to only 40° C., the polymer undergoes a phase transition from amorphous to crystalline, thereby altering the polymer's physical properties. Attempted photolithography was, therefore, performed with careful attention to avoid elevated temperatures, and also omitted the pre-bake step. A photoresist solution was spin-cast on PCLF, and the photoresist solvent was evaporated to cure the layer either by exposure to air flow at room temperature or with a post-bake at 30° C.; PCLF substrates coated with photoresist were then patterned by exposure to UV light under a 30×30 photomask and developed with the standard alkaline developer. After UV exposure and development the photoresist could not be removed to expose the native PCLF; the characteristic structure of PCLF was not revealed when photolithography was performed after curing the photoresist by either evaporation of solvent or after a post-bake at 30° C. Sonication in ethanol—a common procedure for removing photoresist—was ineffective to remove photoresist from the surface; attempts to remove photoresist using other solvents such as acetone, dimethyl sulfoxide, methylene chloride, methanol, or tetrahydrofuran were likewise futile, as the photoresist clearly remained visible upon optical examination after solvent treatment.

Shadow masking is a common technique used for chemical vapor deposition in the fabrication of microelectronics. Shadow masking employs a physical stencil mask through which a volatile chemical is evaporated to form a pattern on a substrate. Vapor deposition through a shadow mask generally requires special equipment to maintain intimate contact between the mask and the substrate so that there is no bleed of chemical vapor around the edges of the mask. Previous attempts to pattern other polymer and silicon substrates through shadow masking evidenced poor adhesion between the mask and the substrate without such specialized mask alignment equipment. When the shadow mask was placed over a silicon or other polymer substrate and treated with vapor of a volatile zirconium alkoxide, the poor adhesion between the mask and the substrates allowed for exposure of the entire substrate surface to vapor; thus, the surface became completely coated with zirconium oxide, rather than confining the surface functionalization to the desired pattern.

The observation that PCLF seemed characteristically "sticky" or "tacky" led to the development of a viable shadow mask-based process for patterning of this polymer. FIG. 1 shows the inventive scheme in which a polymer such as PCLF is mildly heated to enhance the "stickiness" of the surface (step 1). A shadow mask template fabricated by laser ablation of a flexible polyimide (such as KAPTON®) coupon is placed above the PCLF substrate (step 2). The PCLF-mask ensemble is exposed to Zr(O-tBu)$_4$ at $1\times10^{-3}$ torr, then mildly heated to form a mixed zirconium oxide/alkoxide interface in patterns on the surface of PCLF after removal of the mask (step 3); alkoxide ligands are replaced by phosphonate groups after immersion in a solution of 1,4-butanediphosphonic acid (step 4) yielding PCLF functionalized with the patterned ZrO$_2$/phosphonate (ZrO$_2$/SAMP) interface.

Thus, a physical shadow mask was fabricated from KAPTON®: Stripes with targeted dimensions of about 30 μm×30 μm were ablated from a 120 μm thick coupon of KAPTON®. The KAPTON® mask was placed on a PCLF coupon (1 cm×1 cm) after heating the polymer mildly (from room temperature up to about 80° C., preferably up to about 50° C., but not higher than the glass transition temperature of the polymer) to increase "stickiness;" the process of heating PCLF did not change the surface morphology of PCLF once it cooled and returned to the amorphous phase. The mask-PCLF ensemble was then placed in a vapor deposition chamber and volatile zirconium tetra(tert-butoxide) was evaporated through the chamber at $1\times10'$ torr for 30 seconds; Zr(O-tBu)$_4$ coordinates to the oxygen functionalities of the PCLF only where the PCLF surface is exposed through the mask. After mild heating (from room temperature to about 50° C. so as not to deform the pattern), a cross-linked zirconium oxide/alkoxide layer was formed on the PCLF substrate; subsequent immersion in a solution of 1,4-butanediphosphonic acid exchanged the alkoxide ligands for phosphonates yielding the ZrO$_2$/SAMP interface in patterns on the surface. The concentration range of the 1,4-butanediphosphonic acid solution is from about 1 micromolar to about 1 millimolar in an appropriate solvent, with ethanol or methanol being preferred. After rinsing with isopropanol, patterns could be easily observed using an optical microscope.

Scanning electron microscope (SEM) images showed uniform stripes over a large area at low magnification; these stripes were well-defined at high magnification, and were rather smooth compared to the rough, native surface of PCLF. Energy dispersive X-ray spectroscopy (or energy dispersion spectroscopy, "EDS") analysis of the striped pattern indicated that the wider stripe was the bare PCLF and the narrower stripe was the ZrO$_2$/SAMP functionalized area: A point spectrum taken on the more narrow of the stripes showed a Zr (Lα) peak (2.42 keV) while the point spectrum of the wider stripe—having the greater surface roughness—showed no evidence of the Zr (Lα) peak. EDS analysis thus confirmed that the 1,4-butanediphosphonic acid-functionalization was successfully constrained within the pattern. Measurement of the stripe dimensions showed that the 1,4-butanediphosphonic acid-modified stripe was 27 μm wide and the bare PCLF stripe was 35 μm wide.

XP spectra of both clean PCLF and 1,4-butanediphosphonic acid-patterned PCLF were taken to confirm successful functionalization with the ZrO$_2$/SAMP interface; phosphorous could not be detected by EDS because the Zr (Lα) peak (2.42 eV) overlapped with the P (Kα) peak (2.12 eV), and was more intense. While the XP spectrum of clean PCLF showed binding energy (B.E.) peaks that correspond to C(1s) and O(1s) electrons, the XP spectrum of 1,4-butanediphosphonic acid-patterned PCLF indicated the introduction of peaks that corresponded to Zr(3d) and P(2p) electrons. Detailed spectra of the P(2p) peaks for clean PCLF and 1,4-butanediphosphonic acid-patterned PCLF were overlaid; interestingly, a small P(2p) peak at B.E.=132.75 eV was present on the XP spectrum for the clean PCLF sample, which was attributed to the acyl phosphine oxide photoinitiator (IRGACURE 819®) used to cross-link the polymer during fabrication. The XP spectrum of 1,4-butanediphosphonic acid-patterned PCLF showed the introduction a larger, more intense P(2p) peak at B.E.=133.1 eV, which supported successful modification of PCLF with the ZrO$_2$/SAMP interface.

FIG. 2 shows NIH 3T3 fibroblasts spread on shadow mask-patterned PCLF stained for actin after 24 hours (A) and 3 days (B). Fast Fourier transform (FFT) output of the actin images for 24 hours (C) and 3 days (D). Lines through ovals on FFT images represent length and width measurements used to measure aspect ratio, which is indicated at the bottom right. Actin stained with rhodamine phalloidin; scale bar=100 μm. Alignment was quantified on each surface by FFT analysis by measuring the aspect ratio of the FFT output image. The aspect ratio was derived by dividing the vertical dimension of the oval by the horizontal dimension of the oval that is produced by the FFT. The FFT produces an image in which the width of the oval (the horizontal line) is rotated 90° with regard to the (vertical) pattern direction; thus perfect alignment with a pattern that is vertical on the page would generate an FFT that is a perfect horizontal line. Therefore, the longer the horizontal line and the shorter the vertical one (giving the smallest numerical ratio), the better the alignment of the cells with the pattern; perfect alignment would have a ratio of zero.

Figures 2A, 2B, 2C, 2D:
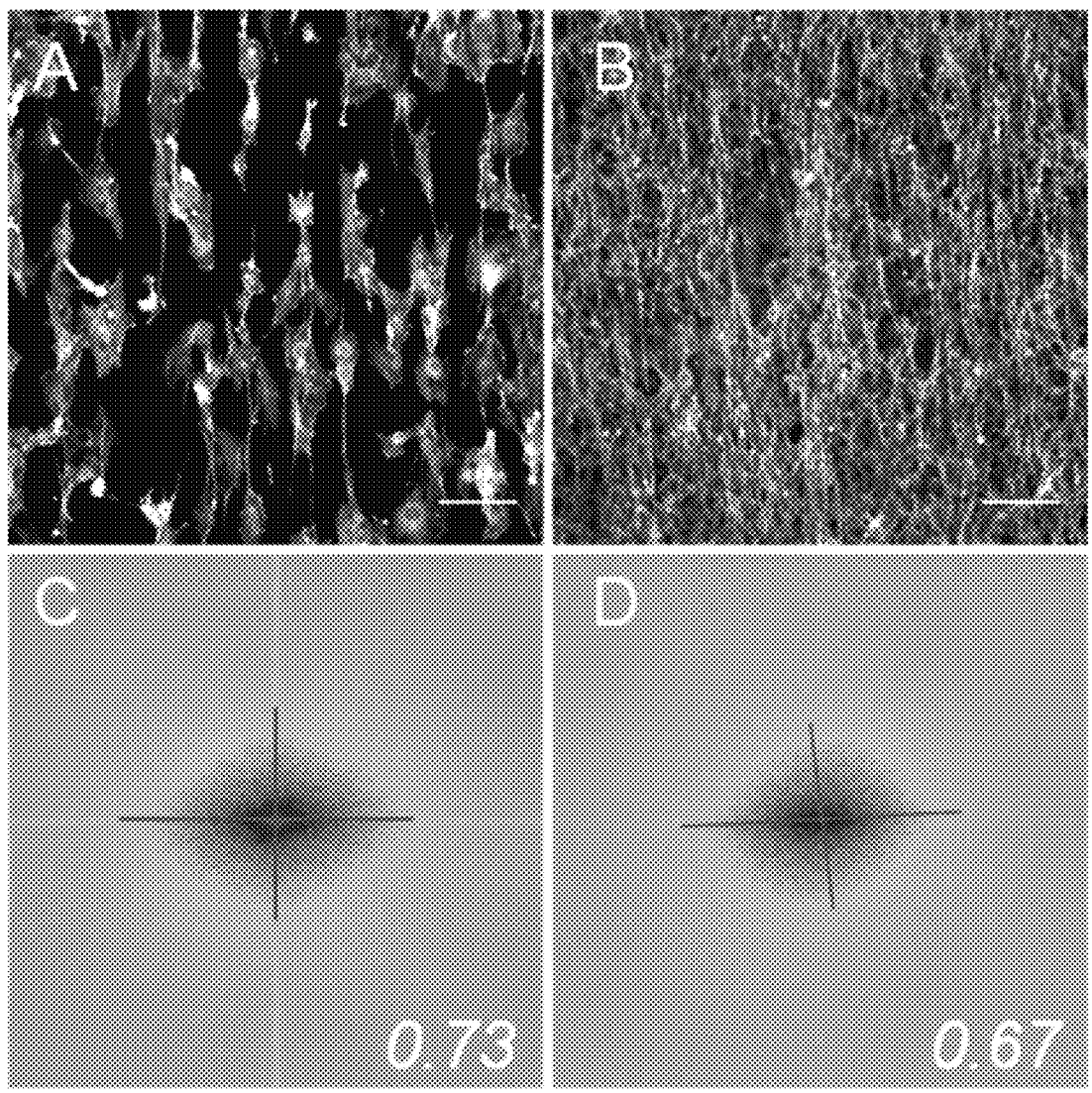
FIGS. 2A, 2B, 2C and 2D show NIH 3T3 fibroblasts spread on shadow mask-patterned PCLF stained for actin after 24 hours (2A) and 3 days (2B). FFT output of the actin images for 24 hours (2C) and 3 days (2D).

Thus, NIH 3T3 cells were plated on 1,4-butanediphosphonic acid-patterned PCLF to evaluate whether the patterned interface could facilitate cell alignment as well as PET, PEEK, and nylon. Cells adhered and spread preferentially with the pattern after 24 hours (FIG. 2A) and proliferated to confluence in alignment with the pattern (FIG. 2B).

Alignment of intracellular actin was analyzed with FFT (FIGS. 2C and D) and quantified by obtaining the aspect ratio of the oval given by the FFT output image. FFT output aspect ratio was derived by dividing the width of the oval by the length of the oval: the smaller the ratio, the better the alignment. FFT output aspect ratios of 0.73 for images of cell actin after 24 hours and 0.67 for images of cell actin after 3 days around the range of the actin image FFT output ratios found for PET, PEEK and nylon (0.68-0.79). Thus, the patterned 1,4-butanediphosphonic acid-interface could be fabricated on PCLF via shadow mask templated cell alignment having analytical parameters the same as the 1,4-butanediphosphonic acid-patterned interface constructed on PET, PEEK, or nylon using photolithography.

FIG. 3 shows fibronectin assembled by 3T3 cells after 3 days on 1,4-butanediphosphonic acid-patterned PCLF (A) and PET (B) substrates; FFT outputs of the actin images from PCLF and PET surfaces are displayed in (C) and (D), respectively. Lines through ovals on FFT images represent length and width measurements used to measure the aspect ratio, which is indicated at the bottom right. The pattern is vertical, fibronectin is stained with R457, and scale bar=100 µm. Alignment was quantified on each surface by fast Fourier transform (FFT) analysis by measuring the aspect ratio of the FFT output image. The aspect ratio was derived by dividing the vertical dimension of the oval by the horizontal dimension of the oval that is produced by the FFT. As noted above, FFT produces an image in which the width of the oval (the horizontal line) is rotated 90° with regard to the (vertical) pattern direction; thus perfect alignment with a pattern that is vertical on the page would generate an FFT that is a perfect horizontal line. Therefore, the longer the horizontal line and the shorter the vertical one (giving the smallest numerical ratio), the better the alignment of the cells with the pattern; perfect alignment would have a ratio of zero.

Figures 3A, 3B, 3C, 3D:
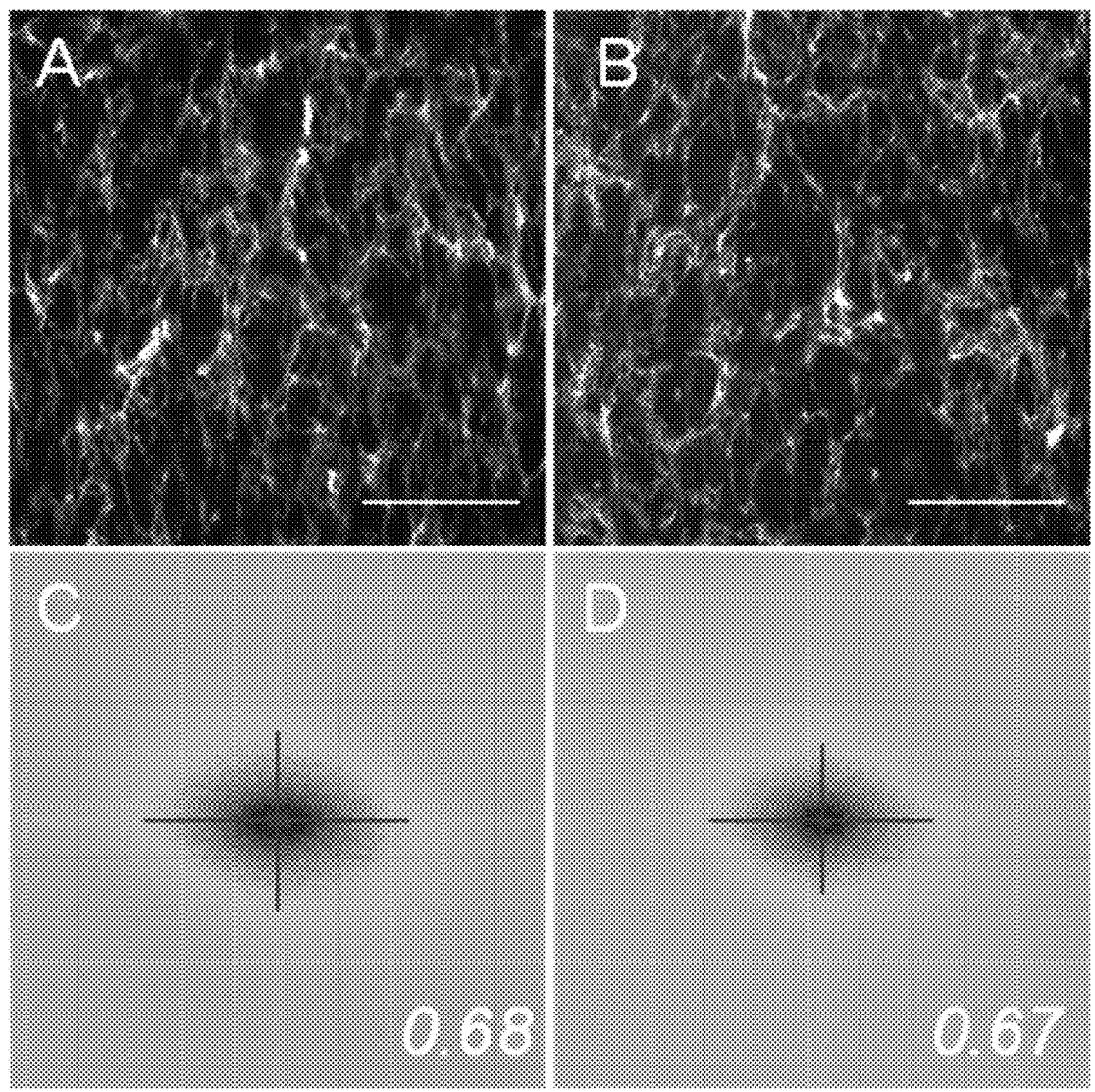
FIGS. 3A, 3B, 3C and 3D show fibronectin assembled by 3T3 cells after 3 days on 1,4-butanediphosphonic acid-patterned PCLF (3A) and PET (3B) substrates; FFT outputs of the actin images from PCLF (3C) and PET (3D) surfaces.

ECM assembly on PCLF patterned with 1,4-butanediphosphonic acid using the shadow mask technique was compared to ECM assembly on photolithographically 1,4-butanediphos-phonic acid-patterned PET. After 3 days, 3T3 cells plated at 50,000 cells/well assembled a fibronectin matrix that was aligned with the pattern on both PCLF (FIG. 3A) and PET (FIG. 3B). Quantification of fibronectin images by FFT yielded ovals with virtually equivalent aspect ratios: 0.68 for PCLF (FIG. 3C) and 0.67 (FIG. 3D). It was clear that $ZrO_2$/SAMP patterns facilitated assembly of aligned fibronectin whether they are constructed on the hard model polymer PET or the softer, more flexible and PNS-compatible material PCLF.

In order to realize the clinical potential of an aligned ECM template as a bridge to guide nerve regeneration, the interface patterning technology that is crucial for achieving aligned cell assembled ECM was translated from PET, a hard polymer incompatible with nerves, to PCLF, a softer polymer designed for PNS applications. The patterning technique of photolithography proved to be incompatible with PCLF; therefore, a surface-conforming shadow masking technique was developed to pattern PCLF with the 1,4-butanediphosphonic acid-interface by taking advantage of the sticky nature of PCLF. Patterns constructed on PCLF using the above-described shadow mask technology provided templated adhesion and proliferation of 3T3 fibroblasts across an entire substrate, and facilitated the assembly of extracellular matrix that is aligned just as well as it is on patterned PET.

Shadow mask patterning proved to be particularly useful for patterning PCLF; it also provided a powerful tool to pattern other materials whose surface chemical or materials properties are incompatible with the reagents or processes of photolithography due to chemical incompatibility with the photolithography reagents (photoresist, solvents, and other chemicals required for the process), or are incompatible due to the physical nature of the surface (e.g., curved versus planar). Another unique benefit of the physical shadow mask is that it adheres to the PCLF surface; the flexibility of a KAPTON® mask allows it to conform to a substrate surface even when the polymer surface is curved.

Figures 4A, 4B, 4C:
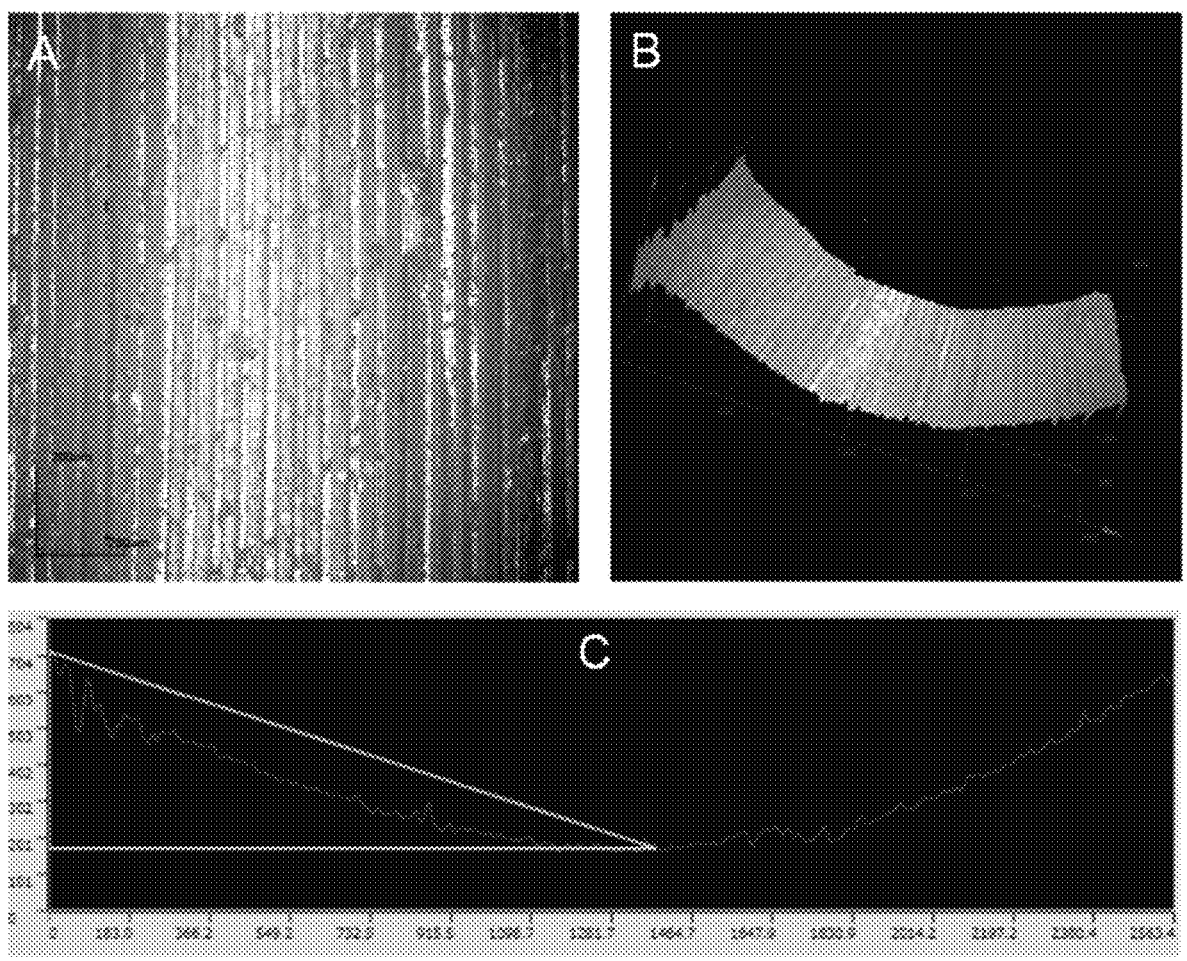
FIGS. 4A, 4B and 4C show the confocal image (4A) of a curved PCLF substrate patterned with 1,4-butanediphosphonic acid via shadow masking; 10× magnification, scale bar=200 μm. 3D rendition of the 5× confocal image (4B) and height profile (4C) illustrate the curvature of the surface; scale bar values for x and y axes in μm.

To examine whether the shadow mask could be used to pattern a curved surface, a mask-PCLF coupon ensemble was curved to fit inside a glass tube of diameter=8 mm; the glass tube was gently heated and tweezers were used to push the PCLF-mask ensemble against the glass, such that it conformed to the shape of the tube. The glass tube-PCLF-mask construct was placed in a chamber and exposed to vapor of $Zr(O-tBu)_4$, mildly heated, and then placed in solution of 1,4-butanediphosphonic acid to form the 1,4-butanediphosphonic acid-interface in stripes on the PCLF surface as described above. When the curved PCLF-mask ensemble was removed from the inside of the glass tube, PCLF maintained its curved structure; when the mask was lifted off the PCLF substrate, patterned stripes were clearly visible upon optical microscopy. A confocal microscope image (FIG. 4A) shows the 1,4-butanediphosphonic acid-patterned interface on a curved PCLF substrate; the 3D rendition of the confocal image (FIG. 4B) and corresponding height profile (FIG. 4C) illustrate that the pattern has been constructed on the concave face of a curved surface.

Patterning can also be done on a scaffold or construct which already has the form of a tube or tube-like structure, or a folded device. The tube or tube-like structure can be a rolled species, a rolled-up system, a preformed tube, or a species of similar geometry. In one embodiment the patterning is on the inside, or interior surface of the tube or tube-like scaffold.

Thus using a flexible shadow mask makes possible patterning on a curved surface, something that cannot be accomplished via traditional lithography-based microfabrication techniques. The shadow mask patterning technology can be applied to other substrate materials that are currently believed to be incompatible as substrates for photolithography for surface reactivity and/or surface geometry reasons. Examples of these incompatible materials include natural polymer scaffolds, such as collagen or silk, or conducting polymers, such as PEDOT:PSS (Poly(EthyleneDiOxyThiophene): Poly(Styrene Sulfonate)); OPF, and PCLF; or hydrogels of poly(ethylene oxide), poly(ethylene glycol), cross-linked poly(acrylic acid), poly(acrylamides), poly (acrylates), sucrose, carbohydrate glass, alginate, chitosan, or chondroitin which are destroyed by the reagents of photolithography.

In one embodiment, the polymer comprises polyamides, polyurethanes, polyureas, polyesters, polyketones, polyimides, polysulfides, polysulfoxides, polysulfones, polythiophenes, polypyridines, polypyrroles, polyethers, silicone (polysiloxanes), polysaccharides, fluoro-polymers, epoxies, aramides, amides, imides, polypeptides, polyethylene, polystyrene, poly-propylene, liquid crystal polymers, thermoplastics, polyvinyls, polyacrylics, polyacrylates, polycarbonates, polytetrafluoroethylene (PTFE), polyethylene terephthalate (PET), poly(vinyl-pyrrolidone), poly(-hydroxyethyl methacrylate), poly(N-vinylpyrrolidone), poly (methyl methacrylate), poly(vinyl alcohol), poly(acrylic acid), polyacrylamide, polyethylene-co-vinyl acetate), poly (ethylene glycol), poly(methacrylic acid), polylactides (PLA), polyglycolides (PGA), poly(lactide-co-glycolides) (PLGA), polylactones, polyanhydrides, polyphosphazenes, polyorthoesters, polyolefins, polycarbonates, aliphatic polyether-based thermoplastic polyurethanes, biopolymers, such as silk, collagen, copolymers and derivatives thereof, and composites including these polymers. In one preferred embodiment, the polymer is a polyetheretherketone, a nylon, including nylon-6,6, or PET. In another embodiment, the polymer is silicone or polyacrylamide. In another preferred embodiment, the polymer is silk or collagen.

Hydrogels are a particularly attractive material for the inventive shadow mask patterning technology in the context of nerve repair. Oligo-(polyethylene glycol) fumarate (OPF), a hydrogel currently under preclinical investigation as a scaffold for spinal cord by the Mayo Clinic, is one such hydrogel. Others include poly(ethylene oxide), poly(ethylene glycol), cross-linked poly(acrylic acid), poly(acrylamides), poly(acrylates), sucrose, carbohydrate glass, alginate, chitosan, and chondroitin. Hydrogels are too mechanically flimsy for spin coating (photolithography process) and are too sensitive to liquid reagents to employ as a substrate for construction of patterned interfaces using photolithographic methods, but are amenable to surface patterning via shadow masking. The flexibility of a polymer shadow mask enables surface conformation of the mask to a hydrogel substrate, and because no photolithography would be required, photolithographic reagents are not absorbed by the gel. A 1,4-butanediphosphonic acid-patterned interface templates the alignment of cell-assembled ECM, such that a device consisting of the scaffold polymer OPF supporting highly-aligned, cell-assembled ECM could be tested for regeneration of a spinal cord injury in vivo.

In vivo testing of PCLF-ECM templates for PNS repair, and OPF-ECM scaffolds for spinal cord injury repair require that these scaffolds can first be tested and optimized in vitro for biological function relative to the nervous system. For example, a co-culture of fibroblasts and Schwann cells may support the construction of a more neurotrophic ECM; additionally, growth factors may need to be added to the ECM to better stimulate neurite outgrowth or neuron survival. Rather than using neuron surrogate PC12 cells, bona fide neurons such as dorsal root ganglion cells can be tested for their response to the patterned ECM. Other suitable neurons and neural cells include neurons from CNS or PNS, neural support cells such as Schwann cells and radial glial cells, neural stem cells such as cells that form neurospheres, and neural tumor cells such as glioblastoma and neuroblastoma cells. A 3D device must also be constructed to match the dimensions of a peripheral nerve or spinal cord; this device can be constructed from stacks of 2D layers of templated ECM, or it can consist of a 2D sheet of patterned ECM rolled into a 3D tube. A nerve regeneration device based on a polymer-ECM bridge can be constructed using the disclosed technology. Specifically, a simple chemical pattern can be constructed on both hard and soft polymer surfaces via substrate-compatible techniques, and that pattern facilitates the assembly of aligned ECM by cells on these patterned surfaces.

In summary, a superior method to control cell alignment on polymers, with targeted application to nerve regeneration, muscle growth/regrowth, and other in vitro and in vivo applications, is now available via patterning of fragile polymer surfaces and/or non-planar surfaces. Previously, photolithography was employed to make the patterns through a multi-step process involving spin-coating a photoresist on the polymer, followed by exposure to UV radiation through a mask, followed by development in alkali. In the present disclosure, a shadow mask (a perforated mask) is placed onto and adhered to the polymer, and the metal alkoxide precursor of the pattern is evaporated onto the polymer; no photolithography is involved, and the shadow mask patterns provide equally good benefits for cell alignment. In one embodiment the metal alkoxide is selected from Zr, Ti, Group 5 or Group 6 metals, where Group 5 metals include V, Nb and Ta, and Group 6 metals include Cr, Mo and W. In one embodiment the metal alkoxide is a zirconium alkoxide. The photo-lithography process of spin-coating a photoresist onto the polymer, followed by exposure to UV radiation through a mask, followed by development in alkali, is no longer required for fragile or non-planar substrates or scaffolds.

The present procedure enables the rapid preparation of templates for nerve regeneration, about 10 times faster than the previously described photolithography methods, and also is amenable to very soft polymers, including hydrogels, and to polymer substrates having curved surfaces.

One aspect of the invention is directed to a polymeric substrate that is incompatible with photolithography conditions, at least a portion of a surface of which comprises a material suitable for cell attachment, in a pattern which is raised above the surface of the substrate. In one embodiment of the polymeric substrate, the raised pattern comprises the polymer of the polymeric substrate. In another embodiment of the polymeric substrate the raised pattern comprises at least one cell-binding or cell-adhesive material. The polymeric substrate can be incompatible with photolithography conditions due to one or more incompatibilities selected from the group consisting of temperature incompatibility, solvent incompatibility, reagent incompatibility, and surface geometry incompatibility. In one embodiment the surface geometry incompatibility comprises surface curvature. In some embodiments the curvature comprises a curved surface selected from the group consisting of inward-curving concave surfaces and outward-curving convex surfaces.

In one embodiment the polymeric substrate is in the form of a tube or a tube-like structure and the raised-patterned surface is on the interior of the tube or tube-like structure. The tube or tube-like structure can be a rolled species, a rolled-up system, a preformed tube, or a species of similar geometry.

Another aspect of the invention is directed to a method of patterning a surface of a polymeric substrate which is incompatible with photolithography conditions, comprising the steps of a) providing a shadow mask, b) applying the shadow mask to a surface of the polymeric substrate to form a masked substrate, c) applying pressure to the shadow mask surface of the masked substrate, optionally with heating sufficient to form a phase transition in the polymer of the polymeric substrate, d) optionally, cooling the masked substrate, and e) removing the mask to reveal a physically patterned polymeric surface. The applied pressure must be sufficient to emboss the polymer surface so that the negative pattern of the shadow mask is formed in the polymer surface. If required, this can be accomplished with simultaneous heating of the polymeric substrate to a softening temperature which depends on the polymer, so that the polymeric substrate is amenable to pressurized embossing.

This process results in raised areas of polymer corresponding to the voids in the shadow mask, providing a physical pattern. The polymeric substrate can be incompatible with photolithography conditions due to one or more incompatibilities selected from the group consisting of temperature incompatibility, solvent incompatibility, reagent incompatibility, and surface geometry incompatibility. In some embodiments the surface geometry incompatibility comprises surface curvature. In some embodiments the patterning is on the inside surface of a tube, a tube-like substrate, or a folded substrate. The tube or tube-like substrate can comprise a rolled species, a rolled-up system, a preformed tube, or a species of similar geometry. In one embodiment the polymeric substrate is a preformed tube having patterning on the inside surface.

For the physically patterned, embossed polymeric substrates, any cell-adhesive material, or a material that becomes cell-adhesive in plasma, can be used to adhere cells to the physical pattern and form the ECM. Such cell-adhesive materials include collagen, fibronectin, and laminin. Example 10, vide infra, discloses internally physically patterned PCLF tubes with an ECM formed using fibronectin.

Yet another aspect of the invention is directed to a method of preparing a shadow mask for patterning the inside surface of a polymeric tube which is incompatible with photolithography conditions, comprising the steps of a) providing a coupon of polymer having a thickness of about 10 µm to about 120 µm, and having appropriate dimensions to completely cover the inside surface of a polymeric tube, and b) ablating the coupon to remove selected segments of the polymer, providing a desired pattern; wherein the coupon polymer is adherent to the interior surface of the polymeric tube such that the peel strength therebetween is less than the tensile strength of either of the coupon polymer or the polymeric tube. In one embodiment of the method the ablation comprises laser ablation. The polymeric tube can be incompatible with photolithography conditions due to one or more incompatibilities selected from the group consisting of temperature incompatibility, solvent incompatibility, reagent incompatibility, and surface geometry incompatibility. In one embodiment the surface geometry incompatibility comprises surface curvature.

Still another aspect of the invention is directed to a construct which supports cell attachment and alignment, comprising a) a substrate which is incompatible with photolithography conditions; b) a patterned coating of a metal alkoxide, oxide or mixed oxide-alkoxide disposed thereon; and c) a phosphonic acid covalently attached to b), which phosphonic acid contains functionality adapted for cell binding. In one embodiment the metal alkoxide is selected from Zr, Ti, Group 5 or Group 6 metals, where Group 5 metals include V, Nb, and Ta, and Group 6 metals include Cr, Mo and W. In one embodiment the metal alkoxide is a zirconium alkoxide. One embodiment of the construct further comprises cells attached thereto. Another embodiment of the construct further comprises an aligned extracellular matrix (ECM). The substrate can be incompatible with photolithography conditions due to one or more incompatibilities selected from the group consisting of temperature incompatibility, solvent incompatibility, reagent incompatibility, and surface geometry incompatibility. In one embodiment the surface geometry incompatibility comprises surface curvature.

Another aspect of the invention is directed to a construct which supports cell attachment and alignment, comprising: a) a substrate which is incompatible with photolithography conditions; and b) a patterned coating of a cell-adhesive compound disposed thereon. In one embodiment the cell-adhesive compound comprises fibronectin. In another embodiment the cell-adhesive compound is fibronectin. In one embodiment the construct further comprises cells attached thereto. In one embodiment the construct further comprises an aligned extracellular matrix (ECM).

In some embodiments of the construct, the phosphonic acid comprises one or more functional groups selected from the group consisting of polyol moieties, sugar alcohol moieties, hydroxyl functional groups, amino functional groups, carboxylic acid functional groups, carboxylate ester functional groups, phosphonic acid functional groups, phosphonate functional groups, ether functional groups, alkyne functional groups, azide functional groups and thiol functional groups. In one embodiment the phosphonic acid is 1,4-butanediphosphonic acid. In some embodiments of the construct the substrate comprises a polymer selected from the group consisting of polyamides, polyurethanes, polyureas, polyesters, polyketones, polyimides, polysulfides, polysulfoxides, polysulfones, polythiophenes, polypyridines, polypyrroles, polyethers, silicone (polysiloxanes), polysaccharides, fluoro-polymers, epoxies, aramides, amides, imides, polypeptides, polyolefins, polyethylene, polystyrene, polypropylene, liquid crystal polymers, thermoplastics, polyvinyls, poly(vinyl alcohol), polyacrylics, polyacrylates, poly (acrylic acid), polycarbonates, polytetrafluoroethylene (PTFE), polyethylene terephthalate (PET), poly(vinyl-pyrrolidone), poly(-hydroxyethyl methacrylate), poly(N-vinylpyrrolidone), poly(methyl methacrylate), polyethylene-co-vinyl acetate), poly(methacrylic acid), polylactides (PLA), polyglycolides (PGA), poly(lactide-co-glycolides) (PLGA), polylactones, polyanhydrides, polyphosphazenes, polyorthoesters, polycaprolactone fumarate (PCLF), oligo-(polyethylene glycol) fumarate (OPF), PEDOT:PSS, poly (ethylene oxide), poly(ethylene glycol), cross-linked poly (acrylic acid), poly(acrylamides), aliphatic polyether-based thermoplastic polyurethanes, sucrose, carbohydrate glass, biopolymers such as silk, collagen, alginate, chitosan, and chondroitin, copolymers and derivatives thereof, and composites including these polymers. In preferred embodiments the substrate polymer comprises PCLF, OPF, or an aliphatic polyether-based thermoplastic polyurethane. In a preferred embodiment the substrate polymer is PCLF. In another preferred embodiment the substrate polymer is OPF. In a further preferred embodiment the substrate polymer is an aliphatic polyether-based thermoplastic polyurethane, such as TECOFLEX™ EG-80A.

In one embodiment of the construct, the patterned coating is on the inside surface of a tube, a tube-like substrate, or a folded substrate. The tube or tube-like substrate can comprise a rolled species, a rolled-up system, a preformed tube, or a species of similar geometry.

Another aspect of the invention is directed to a method of preparing a construct which supports cell attachment and alignment, the method comprising a) providing a substrate which is incompatible with photolithography conditions; b) preparing a shadow mask template consisting of a material which is adherent to the substrate such that the peel strength is less than the tensile strength of the shadow mask and substrate material; and c) adhering the shadow mask template to the substrate to form a substrate-mask ensemble. One embodiment of the method further comprises d) exposing the substrate-mask ensemble to a metal alkoxide to form a treated substrate-mask ensemble; e) warming the treated ensemble and removing the mask from the treated substrate-mask ensemble to form a metal oxide/alkoxide patterned surface; and f) covalently attaching to the patterned surface a phosphonic acid containing functionality adapted for cell binding, to form the construct. In one embodiment the metal alkoxide is selected from Zr, Ti, Group 5 or Group 6 metals, where Group 5 metals include V, Nb and Ta, and Group 6 metals include Cr, Mo and W. In one embodiment the metal alkoxide is a zirconium alkoxide.

Another embodiment of the method further comprises d) formation of a raised patterned surface by application of pressure, and optionally heat, to the substrate-mask ensemble; e) removing the mask from the substrate-mask ensemble to expose the raised patterned surface; and f)

exposing the raised patterned surface to a cell-adhesive biomaterial to form the construct. For example, the unmasked patterned substrate can be exposed directly to a cell-adhesive biomaterial such as fibronectin. Other embodiments further comprise the step of attaching cells to the construct. Still other embodiments further comprise the step of incubating the construct to form an aligned extracellular matrix (ECM). The substrate can be incompatible with photolithography conditions due to one or more incompatibilities selected from the group consisting of temperature incompatibility, solvent incompatibility, reagent incompatibility, and surface geometry incompatibility. In one embodiment the surface geometry incompatibility comprises surface curvature. In some embodiment of the method the substrate comprises a tube, a tube-like, or a folded structure and wherein the inside surface of the substrate is patterned. The tube or tube-like structure can comprise a rolled species, a rolled-up system, a preformed tube, or a structure of similar geometry.

In some embodiments of the method the phosphonic acid comprises one or more functional groups selected from the group consisting of polyol moieties, sugar alcohol moieties, hydroxyl functional groups, amino functional groups, carboxylic acid functional groups, carboxylate ester functional groups, phosphonic acid functional groups, phosphonate functional groups, ether functional groups, alkyne functional groups, azide functional groups and thiol functional groups. In one preferred embodiment the phosphonic acid is 1,4-butanediphosphonic acid. In some embodiments of the method the substrate comprises a polymer selected from the group consisting of polyamides, polyurethanes, polyureas, polyesters, polyketones, polyimides, polysulfides, polysulfoxides, polysulfones, polythiophenes, polypyridines, polypyrroles, polyethers, silicone (polysiloxanes), polysaccharides, fluoro-polymers, epoxies, aramides, amides, imides, polypeptides, polyolefins, polyethylene, polystyrene, polypropylene, liquid crystal polymers, thermoplastics, polyvinyls, poly(vinyl alcohol), polyacrylics, polyacrylates, poly(acrylic acid), polycarbonates, polytetrafluoroethylene (PTFE), polyethylene terephthalate (PET), poly(vinyl-pyrrolidone), poly(-hydroxyethyl methacrylate), poly(N-vinylpyrrolidone), poly(methyl methacrylate), polyethylene-co-vinyl acetate), poly(methacrylic acid), polylactides (PLA), polyglycolides (PGA), poly(lactide-co-glycolides) (PLGA), polylactones, polyanhydrides, polyphosphazenes, polyorthoesters, polycaprolactone fumarate (PCLF), oligo-(polyethylene glycol) fumarate (OPF), PEDOT:PSS, poly(ethylene oxide), poly(ethylene glycol), cross-linked poly(acrylic acid), poly(acrylamides), aliphatic polyether-based thermoplastic polyurethanes, sucrose, carbohydrate glass, biopolymers such as silk, collagen, alginate, chitosan, and chondroitin, copolymers and derivatives thereof, and composites including these polymers.

In one preferred embodiment the substrate polymer comprises PCLF, OPF or an aliphatic polyether-based thermoplastic polyurethane. In a preferred embodiment the substrate polymer is PCLF. In a preferred embodiment the substrate polymer is OPF. In a preferred embodiment the substrate polymer is an aliphatic polyether-based thermoplastic polyurethane, such as TECOFLEX™ EG-80A.

One aspect of the invention is directed to a scaffold or construct which supports cell attachment and alignment, comprising a) a substrate which is incompatible with photolithography conditions; b) a patterned coating of a metal alkoxide, oxide or mixed oxide-alkoxide thereon; and c) a phosphonic acid covalently attached to b), which phosphonic acid contains functionality adapted for cell binding. In one embodiment the metal alkoxide is selected from Zr, Ti, Group 5 or Group 6 metals, where Group 5 metals include V, Nb and Ta, and Group 6 metals include Cr, Mo and W. In one embodiment the metal alkoxide is a zirconium alkoxide. In one embodiment the scaffold or construct further comprises cells attached thereto. Preferably, these cells are attached via a phosphonic acid residue or linker, which phosphonic acid has the formula (I):

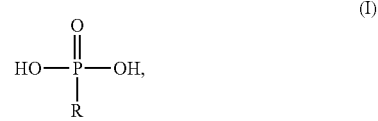

where attachment to the metal alkoxide is via the phosphonate head unit, and attachment of the cells is via the organic tail moiety R of the phosphonic acid residue. The R group can be selected from the group consisting of alkyl, heteroalkyl, alkenyl, heteroalkenyl, alkynyl, heteroalkynyl, aryl, arylalkyl, heteroaryl, and heteroarylalkyl, where heteroalkyl, heteroalkenyl, heteroalkynyl, heteroaryl and heteroarylalkyl contain one or more heteroatoms selected from the group consisting of O, N and S. The R group can be optionally substituted (vide infra). In one embodiment the scaffold or construct further comprises an aligned extracellular matrix (ECM). In one embodiment the substrate is incompatible with photolithography conditions by virtue of one or more incompatibilities selected from the group consisting of temperature incompatibility, solvent incompatibility, reagent incompatibility, and surface geometry incompatibility.

For the purposes of the present application, temperature incompatibility means heating to a temperature above the melting point, or decomposition point, or softening temperature of the polymer or hydrogel so that degradation or some other irreversible change occurs such that the polymer or hydrogel fails to provide a useful scaffold; solvent incompatibility means that erosion, degradation or some other change occurs such that the polymer or hydrogel fails to provide a useful scaffold; reagent incompatibility means that adsorption, absorption, degradation, contamination or some other change occurs such that the polymer or hydrogel fails to provide a useful scaffold. Surface geometry incompatibility means that the surface is formed such that the shadow mask fails to adhere evenly to the surface and therefore fails to provide distinct patterning when the substrate-mask ensemble is exposed to $Zr(O-tBu)_4$, or other metalating agent. This is characteristic of a curved surface or the inside surface of a tube, where a photoresist cannot be applied uniformly. In one preferred embodiment the surface geometry incompatibility comprises surface curvature, either convex or concave.

In one embodiment the phosphonic acid comprises one or more functional groups selected from the group consisting of polyol moieties, sugar alcohol moieties, hydroxyl functional groups, amino functional groups, carboxylic acid functional groups, carboxylate ester functional groups, phosphonic acid functional groups, phosphonate functional groups, ether functional groups, alkyne functional groups, azide functional groups and thiol functional groups; preferably as substituents on the organic moiety R. In a preferred embodiment at least one functional group is attached to the omega-position of R. These functional groups are useful for linking cells and the ECM matrix to the scaffold or construct. R can also be further substituted with one or more alkyl, alkoxy, halo or hydroxy groups. In one embodiment the phosphonic acid is 1,4-butanediphosphonic acid, where the functional group of the phosphonic acid discussed above is a phosphonic acid functional group.

In one embodiment the substrate comprises a polymer selected from the group consisting of polyamides, polyurethanes, polyureas, polyesters, polyketones, polyimides, polysulfides, polysulfoxides, polysulfones, polythiophenes, polypyridines, polypyrroles, polyethers, silicone (polysiloxanes), polysaccharides, fluoro-polymers, epoxies, aramides, amides, imides, polypeptides, polyolefins, polyethylene, polystyrene, poly-propylene, liquid crystal polymers, thermoplastics, polyvinyl s, poly(vinyl alcohol), polyacrylics, polyacrylates, poly(acrylic acid), polycarbonates, polytetrafluoroethylene (PTFE), polyethylene terephthalate (PET), poly(vinyl-pyrrolidone), poly(-hydroxyethyl methacrylate), poly(N-vinylpyrrolidone), poly(methyl methacrylate), polyethylene-co-vinyl acetate), poly(methacrylic acid), polylactides (PLA), polyglycolides (PGA), poly(lactide-co-glycolides) (PLGA), polylactones, polyanhydrides, polyphosphazenes, polyorthoesters, polycaprolactone fumarate (PCLF), oligo-(polyethylene glycol) fumarate (OPF), PEDOT:PSS, poly(ethylene oxide), poly(ethylene glycol), cross-linked poly(acrylic acid), poly(acrylamides), aliphatic polyether-based thermoplastic polyurethanes, sucrose, carbohydrate glass, biopolymers such as silk, collagen, alginate, chitosan, and chondroitin, copolymers and derivatives thereof, and composites including these polymers. In a preferred embodiment the polymer is selected from the group consisting of polycaprolactone fumarate (PCLF), oligo-(polyethylene glycol) fumarate (OPF), an aliphatic polyether-based thermoplastic polyurethane (such as TECOFLEX™ EG-80A), collagen, silk and PEDOT:PSS. PEDOT:PSS is a common conducting organic polymer, consisting of two components, Poly(EthyleneDiOxy-Thiophene), a cationic material, and Poly(Styrene Sulfonate), the counter anion. In one preferred embodiment the substrate polymer is PCLF. Another preferred embodiment of the substrate polymer is OPF. A further preferred embodiment of the substrate polymer is aliphatic polyether-based thermoplastic polyurethane, such as TECOFLEX™ EG-80A.

Another aspect of the invention is directed to a method of preparing a construct which supports cell attachment and alignment, the method comprising a) providing a substrate which is incompatible with photolithography conditions; b) preparing a shadow mask template consisting of a material which is adherent to the substrate such that the peel strength is less than the tensile strength of the shadow mask and substrate material; c) adhering the shadow mask template to the substrate to form a substrate-mask ensemble; d) exposing the substrate-mask ensemble to a metal alkoxide to form a treated substrate-mask ensemble; e) removing the mask from the treated substrate-mask ensemble to form a metal oxide/alkoxide patterned surface; and f) covalently attaching to the patterned surface a phosphonic acid containing functionality adapted for cell binding, to form the scaffold or construct. In one embodiment the metal alkoxide is selected from Zr, Ti, Group 5 or Group 6 metals. In one embodiment the metal alkoxide is a zirconium alkoxide.

The shadow mask template can be made to contact the substrate by factors including the gravitational force of the mask over the substrate, and/or the physical adhesion between the mask and the substrate such that the peel strength is less than the tensile strength of the shadow mask and substrate materials. In one embodiment the method further comprises g) attaching cells to the construct. In one embodiment the method further comprises h) incubating the construct to form an aligned extracellular matrix (ECM). In a preferred embodiment of the method, the substrate is incompatible with photolithography conditions by virtue of one or more incompatibilities selected from the group consisting of temperature incompatibility, solvent incompatibility, reagent incompatibility, and surface geometry incompatibility.

In one embodiment the surface geometry incompatibility comprises surface curvature. Another embodiment of the surface geometry incompatibility comprises the inside surface of a tubular substrate. In another preferred embodiment of the method, the phosphonic acid comprises one or more functional groups selected from the group consisting of polyol moieties, sugar alcohol moieties, hydroxyl functional groups, amino functional groups, carboxylic acid functional groups, carboxylate ester functional groups, phosphonic acid functional groups, phosphonate functional groups, ether functional groups, alkyne functional groups, azide functional groups and thiol functional groups.

In one embodiment of the method, the phosphonic acid is 1,4-butanediphosphonic acid. In one embodiment of the method, the substrate comprises a polymer selected from the group consisting of polycaprolactone fumarate (PCLF), oligo-(polyethylene glycol) fumarate (OPF), an aliphatic polyether-based thermoplastic polyurethane (such as TECOFLEX™ EG-80A), collagen, silk, PEDOT:PSS, poly(ethylene oxide), poly(ethylene glycol), cross-linked poly(acrylic acid), poly(acrylamides), poly(acrylates), sucrose, carbohydrate glass, alginate, chitosan, and chondroitin. In a preferred embodiment of the method, the substrate polymer is PCLF. In another preferred embodiment the substrate polymer is OPF. In a further preferred embodiment the substrate polymer is an aliphatic polyether-based thermoplastic polyurethane, preferably TECOFLEX™ EG-80A.

Definitions

In the present application the term "fragile" indicates chemical or physical incompatibility with the reagents, and/or solvents, and/or processes involved in photolithography. This can include incompatibility with the photoresist itself or other reagents and/or solvents involved in photolithography. This can also include incompatibility with the conditions of the process, such as heating to a temperature above the melting point, or decomposition point, or softening temperature of the polymer or hydrogel. In the present application the term "incompatible" means causing negative interactions or effects so that the scaffold-forming process fails to produce a scaffold, or the resulting scaffold fails to be useful for its intended purpose or fails to lead to the intended outcome.

Poly(ethylene glycol) (PEG), poly(ethylene oxide) (PEO), or polyoxyethylene (POE) refers to an oligomer or polymer of ethylene oxide. The three names are chemically synonymous, but historically PEG has tended to refer to oligomers and polymers with a molecular mass below 20,000 g/mol, PEO to polymers with a molecular mass above 20,000 g/mol, and POE to a polymer of any molecular mass.

EXAMPLES

General.

PCLF substrates were acquired from Dr. Huan Wang (Mayo Clinic); isopropanol, formaldehyde, 4',6-diamidino-2-phenylindole (DAPI) (Sigma-Aldrich); zirconium tetra (tert-butoxide), Zr(O-tBu)$_4$ (Strem Chemicals, Inc.); 1,4-butanediphosphonic acid (Acros Organics); phosphate buffered saline (PBS), rhodamine phalloidin (Invitrogen); trypsin, versene (LifeTech); Dulbecco's modified eagle medium (DMEM), bovine calf serum (BCS) (Hyclone); nonylhenoxypolyethoxylethanol (NP-40) (EMD Chemicals); and 200 proof ethanol (Pharmco-Aaper) were used as received. NIH 3T3 fibroblasts were maintained in DMEM supplemented with 10% BCS (v/v) and passaged 1:10 by volume twice each week. Trypsin was added to versene before using it to lift cells off tissue culture plates. KAPTON® polyimide film (DuPont) is poly(4,4'-oxydiphenylene-pyromellitimide).

Example 1. XPS Characterization

Polymer surfaces functionalized with patterns of 1,4-butanediphosphonic acid were analyzed by X-ray photoelectron spectroscopy (XPS). A VG scientific ESCALab Mk II equipped with a Mg Kα (1253.6 keV) anode source operating at 15 keV accelerating voltage and 20 mA, and a VG scientific hemispherical sector analyzer (HAS) detector was used. A 50 eV pass energy, 1 eV step size, and 100 ms dwell time were used to collect survey (1000 to 0 eV) spectra. Detailed XPS data were collected at a pass energy of 20 eV with a dwell time of 500 ms and a step size of 0.05 eV. Data analysis was carried out using CasaXPS software (Casa Software Ltd.). Spectra were calibrated against adventitious C is (284.5 eV).

Example 2. SEM and EDS Analysis

Polymer substrates were characterized with a FEI Quanta 200 Environmental-SEM equipped with an Oxford INCA Synergy 450 energy-dispersive X-ray microanalysis system with an X-Max 80 large area analytical silicon drift detector (SDD) at an acceleration voltage of 5 keV. SEM and EDS were performed in low-vacuum mode (0.53 torr) to avoid melting of the polymer by the electron beam.

Example 3. Shadow-Mask Adhesion to PCLF

PCLF coupons were rinsed with isopropanol and dried under a stream of nitrogen. Coupons were placed on a glass slide on a hot plate at 45° C. to heat the coupons slowly. The progress of PCLF phase transition from amorphous to crystalline occurred over about 30 seconds, and could be observed visually as the substrate changed from white and opaque to clear and translucent. Once the phase transition was complete, the glass slide was removed from the hot plate and the KAPTON® shadow mask was placed on the PCLF substrate. The two sides of the KAPTON® were distinct, so careful attention was paid to ensure that the side with stripes of the target pattern dimension contacted the PCLF coupon. Once the mask was placed on the PCLF substrate, it was gently pushed against the polymer with tweezers to achieve optimal adhesion. Mask adhesion occurred similarly for the curved PCLF, with the only exception being that PCLF was heated inside a glass tube such that the polymer was pushed to conform to the glass tube.

Example 4. Vapor Phase Deposition of Zr(O-tBu)$_4$ and Formation of 1,4-Butanediphosphonic Acid-Patterned PCLF PCLF-shadow mask and glass tube-PCLF-shadow mask ensembles were placed inside a deposition chamber equipped with two valves; one was connected to vacuum and the other to a bulb containing Zr(O-tBu)$_4$. The chamber was evacuated to $1 \times 10^{-3}$ torr for 10 min. Samples were exposed to vapor of Zr(O-tBu)$_4$ for 30 sec with the chamber opened to vacuum. The bulb and chamber were sealed; the chamber was wrapped with heat tape and was warmed to 35° C. The chamber was then cooled to room temperature and subsequently evacuated to $1 \times 10^{-3}$ torr for 5 min. After evacuation, the chamber was closed to vacuum and backfilled with zero-grade nitrogen. After closing the valves of both sides of the chamber, the chamber was removed from the vacuum line. The substrates were quickly removed from the chamber and placed in individual vials containing a solution of 1,4-butanediphosphonic acid in ethanol (0.25 mg/mL) for 16 hr to yield polymer films functionalized with 1,4-butanediphosphonic acid. It should be noted that formation of the phosphonate monolayer occurs within minutes of immersion in phosphonic acid solution, so the full 16 hour soak may not be necessary. Substrates were then rinsed with isopropanol, dried under nitrogen, and then assessed by optical microscopy.

Example 5. Cell Alignment on Patterned PCLF Substrates

NIH 3T3 fibroblasts were plated at 50,000 cells per well on 1,4-butanediphosphonic acid-patterned polymer substrates. Cells were fixed at time points of 24 hours and 3 days using 3.7% formaldehyde in PBS for 15 min, permeabilized with 0.5% NP-40 (v/v) in PBS for 15 min at room temperature; cell actin was stained with rhodamine-phalloidin (1:40) and cell nuclei were stained with DAPI (1:1000). Antibodies were diluted by volume in PBS containing 2% BSA. Cells were plated on all surfaces in duplicate. Cells were visualized with a Nikon TE2000U fluorescent microscope and images were captured with a QImaging Retiga 1300 camera and iVision software, and were further analyzed using ImageJ software. Fast Fourier transform (FFT) analysis of actin alignment was performed on 10× actin images that were cropped to make a perfect square of 1024×1024 pixels. Image contrast was normalized with pixel saturation set to 0.4%, and the FFT operation was performed by Image J software. The gray scale output was colorized with the "spectrum" table.

Example 6. Fibronectin Alignment on PET and PCLF Substrates

NIH 3T3 cells were plated at 50,000 cells/well, as described above, on 1,4-butanediphosphonic acid-patterned PET and PCLF substrates. After 3 days, cells were fixed using 3.7% formaldehyde in PBS for 15 min and stained with R457 (1:100) for 30 minutes. After rinsing with PBS, cells were incubated in AlexaFluor 488 (1:400) goat-anti-rabbit secondary IgG. Antibodies were diluted by volume in PBS containing 2% BSA. Fibronectin was visualized by fluorescent microscopy; FFT analysis was performed as described above.

Example 7. Developing a Method of Patterning the Inside Surface of PCLF Tubes 7.1 Methods and Rationale After demonstrating that shadow masking could be used to pattern curved surfaces, the ability of these shadow masks to form a complete pattern on the inside of PCLF tubes of internal diameter 3.5 mm was demonstrated. Patterning the inside of a tube has not successfully been done before and posed new challenges beyond patterning a curved surface. A new method of shadow mask adhesion was needed, because placing the PCLF tubes on a hot plate and heating them through a phase change might deform the shape of the tube. Creating patterns on tubes of this diameter was important for developing and mastering the method of adhesion and to enable confirmation of functionalization via XPS analysis, which might not be possible on the tubes of smaller diameter because of the large angle of curvature.

The new method of adhesion is as follows: shadow masks were manually rolled and inserted into tubes before PCLF is made sticky, in order to ensure proper shadow mask placement. Nichrome wire heated by passage of electrical current was applied in order to mildly heat the mask and PCLF surface from the inside so as to allow the PCLF to become sticky and the mask to adhere without causing the external surface of the tube to undergo a phase change and deform. Once proper adhesion was attained, zirconium tetra(tert-butoxide) was deposited onto the surface and alkoxide ligands were exchanged for phosphonate as described above. Placing the surface in the phosphonate-ethanol solution also weakens adhesion of the shadow mask to the PCLF and allows for removal of the shadow mask without damage to the inside of the PCLF tube or to the newly formed chemical pattern.

7.2 Shadow Masking of PCLF Tubes

Figure 5:
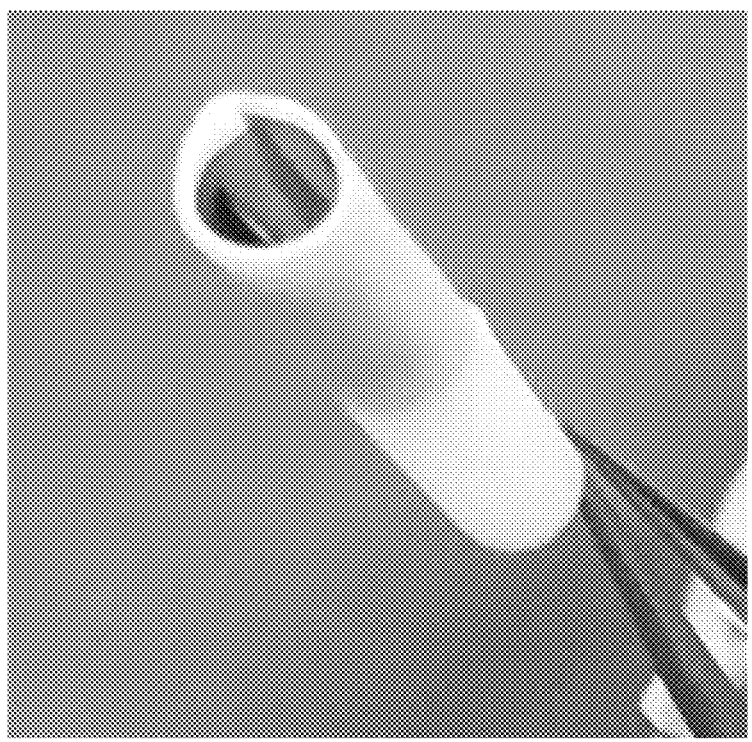
FIG. 5 shows a KAPTON® shadow mask adhered inside a 3.5 mm internal diameter (ID) PCLF tube. KAPTON® polyimide film (DuPont) is poly(4,4'-oxydiphenylene-pyromellitimide).

PCLF tubes of internal diameter 3.5 mm and 1.5 mm were prepared and cleaned by rinsing in isopropanol and drying under nitrogen. Shadow masks of target dimensions 30 μm×30 μm with a width optimized for the 1.5 mm ID tubes were created through laser ablation of KAPTON®. Shadow masks were rolled manually and inserted into 3.5 mm tubes, or rolled around an 18 gauge needle and inserted into 1.5 mm tubes. Masks were adhered to PCLF by inserting a Nichrome wire into the tube, which was heated by passage of electrical current, and applying pressure to the shadow mask until the PCLF phase transition could be identified visually (white to colorless) at which point it was sticky enough to enable adhesion of the KAPTON® shadow mask. An image of a shadow mask inside a 3.5 mm internal diameter PCLF tube is shown in FIG. 5.

7.3 Cell Studies on PCLF Tubes

NIH 3T3 cells were suspended in DMEM growth media with serum (10% BCS) at a dilution of 250,000 cells/mL. PBS was used to rinse patterned PCLF tubes three times. Tubes were securely placed into the opening of a 200 μL micropipette tip. The ensemble was then placed into a 1.5 mL Eppendorf centrifuge tube in order to allow for rotation of the PCLF tube, ensuring cell adhesion on all sides. Cell solution was injected directly inside the PCLF tube until the Eppendorf tube was full. The Eppendorf tube was then laid horizontally on a tube rotator and allowed to turn for 1.5 hours to allow for cell adhesion. The PCLF tube was removed and placed in 1.5 mL of serum-containing media for 2 days. The cells were then fixed, permeabilized, and stained for actin using the same reagents described for flat PCLF by pipetting reagents into the tube. Fluorescence microscopy was used to image longitudinally sliced tubes.

7.4 Results and Discussion

Figure 6A:
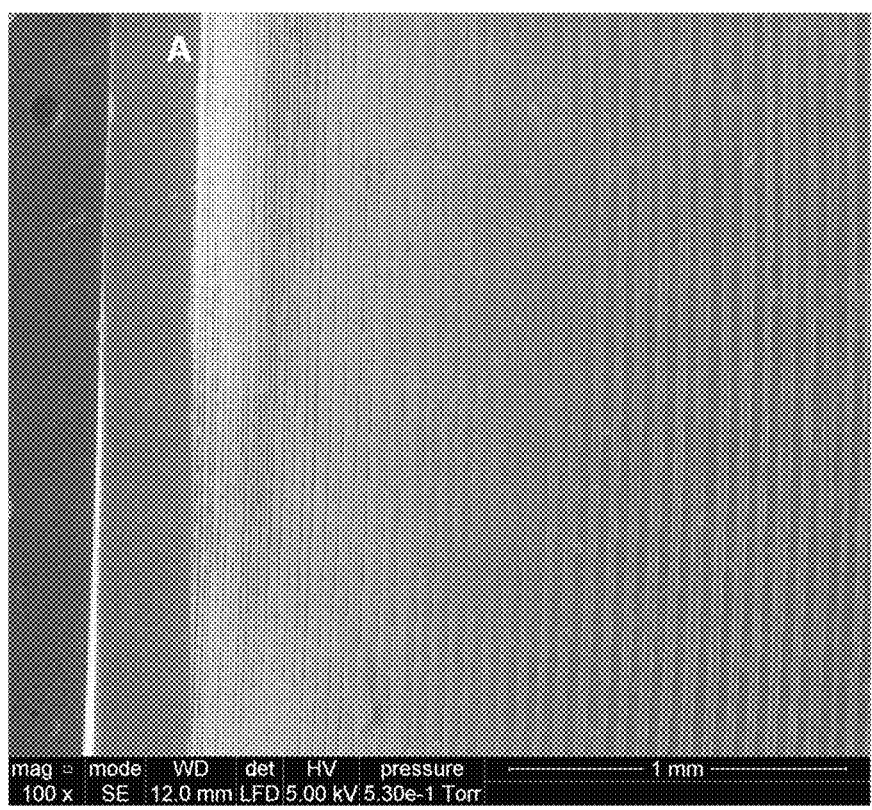
FIGS. 6A and 6B show SEM images of internally patterned 3.5 mm PCLF tubes. (6A) 100× magnification, (6B) 1000× magnification.
Figure 6B:
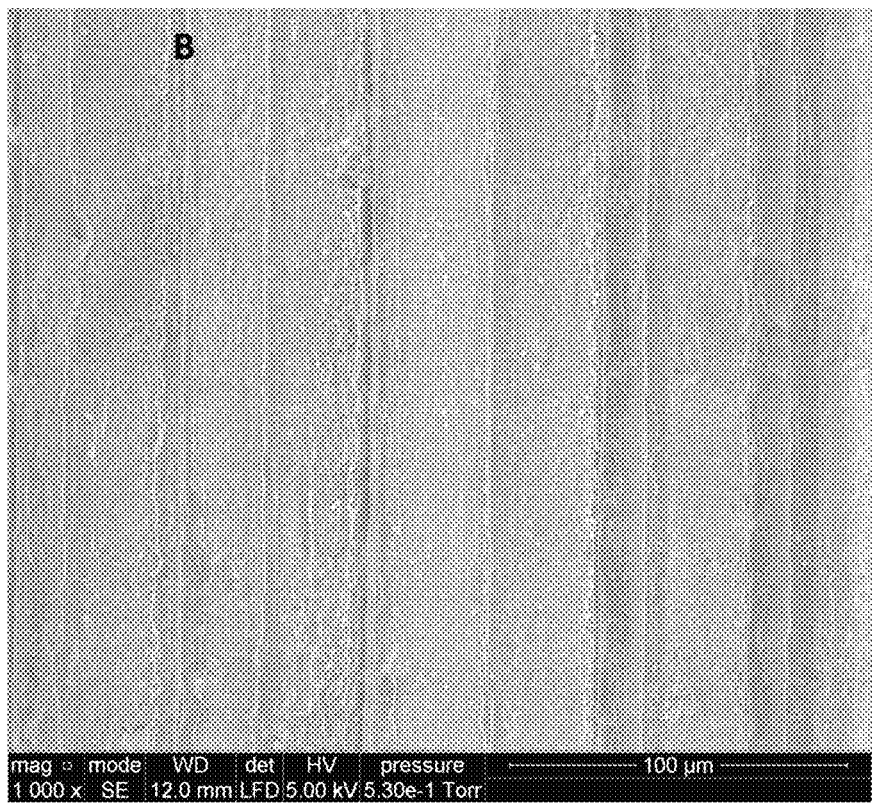

XPS analysis confirmed $ZrO_2$-phosphonate ($ZrO_2$-SAMP) binding. The unpatterned surface showed peaks for O(1s) at 557.5 eV and C(1s) at 284.5 eV. Patterning the surface yielded peaks for Zr(3d) at 183.5 eV, Zr(3p) at 347.5 eV and 333.5 eV, and P(2p) at 133.5 eV. The unpatterned surface also showed a peak for F(1s) at 688.5 eV that was not present on the patterned surface. This peak likely represents a product formed during PCLF creation that was eliminated by the surface modification method. SEM images of patterned tubes showed uniform stripes over the entire surface (FIG. 6).

Figure 7:
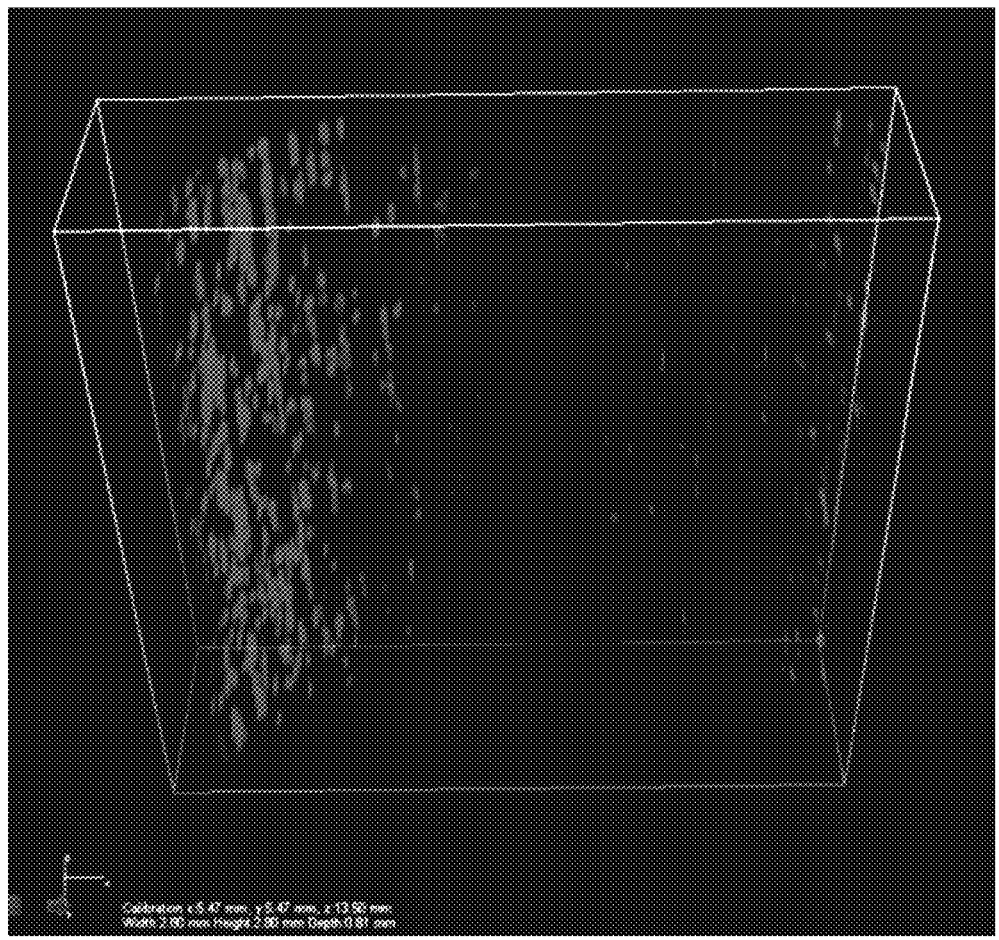
FIG. 7 shows the fluorescent confocal microscopy image of actin aligned in cells on a longitudinally sliced internally patterned 3.5 mm PCLF tube. Actin is stained in this image.

3T3 Fibroblast cells were plated inside this tube by injection directly into the tube and continuous rotation and were shown to align with the pattern. A fluorescent confocal microscopy image of cells aligned along the $ZrO_2$-SAMP stripes on the inside of the patterned PCLF tube is shown in FIG. 7. Actin is stained in this image.

PCLF tubes of 3.5 mm ID were successfully patterned using the present method of shadow masking. The inside of a narrow tube can be patterned via shadow masking and chemical vapor deposition (CVD). When tubes were rotated during cell plating, cells were shown to attach to all sides of the inside of this tube and thus ECM construction will not be constrained to one side of the tube by gravity. Cell alignment along the $ZrO_2$-SAMP stripes showed that this polymer-chemical substrate can direct the growth of fibroblast cells and can also direct the growth of the ECM that these cells construct. It is believed that this is the first example of chemically patterning the inside of a pre-formed tube. The presently disclosed chemical pattern aligns cells not only on flat surfaces but in tubes as well; indicating that aligned ECM can be generated inside a tube.

Example 8. Translating Patterning to PCLF Tubes for Clinical Application 8.1 Methods and Rationale The method of patterning the inside of PCLF tubes described above was translated to tubes with a much smaller internal diameter (e.g., ID=1.5 mm or less), which can be used for clinical studies such as animal tests, including a rat sciatic nerve model. KAPTON® masks of the appropriate dimensions to cover the entire inner surface were prepared. Patterning these smaller tubes posed further challenges in shadow mask preparation and insertion. Furthermore, such small tubes are thinner, and a method of heating through the polymer phase transition without completely melting and deforming the tubes needed to be developed. Proper placement of the shadow masks was achieved by rolling the mask around an 18 gauge needle and inserting the needle/shadow mask ensemble into the PCLF tube. Passage of current through the Nichrome wire was then used to carefully heat the inside of the PCLF tube in order to allow the shadow mask to adhere. Once adhesion was attained, zirconium tetra(tert-butoxide) was deposited and alkoxide ligands were exchanged for phosphonate as described above.

Alternatively, after heating the shadow mask/PCLF tube ensemble with nichrome wire followed by cooling, the shadow mask could be removed (without any chemical treatment) to reveal a physically patterned or textured PCLF tube where the interior polymer surface retains the pattern of the shadow mask as a negative image. This physical patterning of the polymer surface is also referred to herein as "embossing".

8.2 Results and Discussion

Figure 8A:
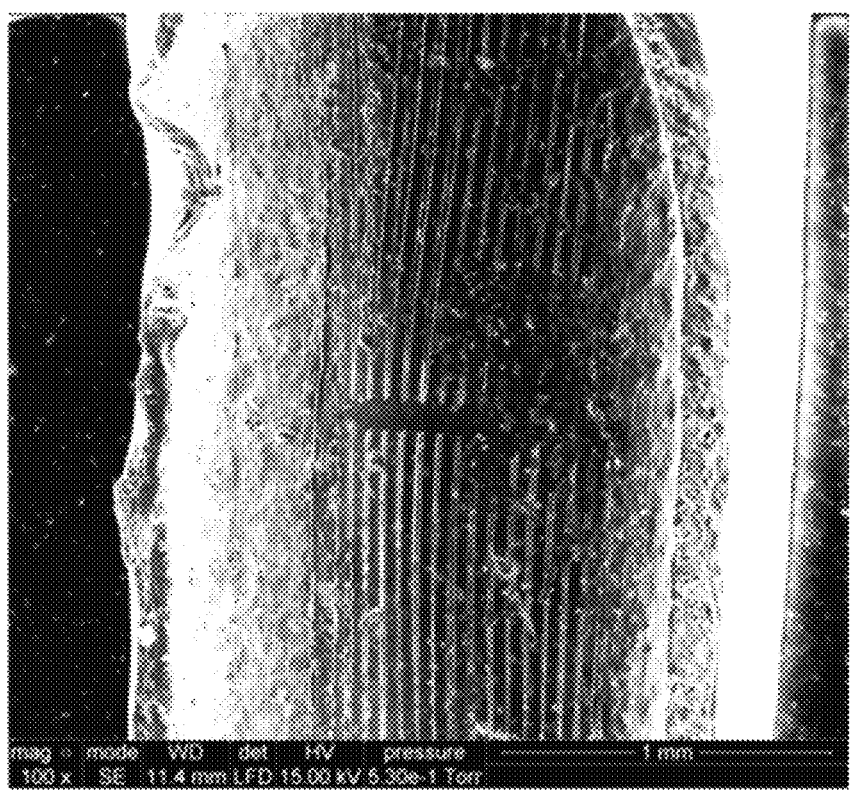
FIGS. 8A and 8B show SEM images of an internally patterned 1.5 mm PCLF tube. (8A) 100× magnification, (8B) 1500× magnification. The gap in the pattern in (A) was created by a structural reinforcement band on the shadow mask.
Figure 8B:
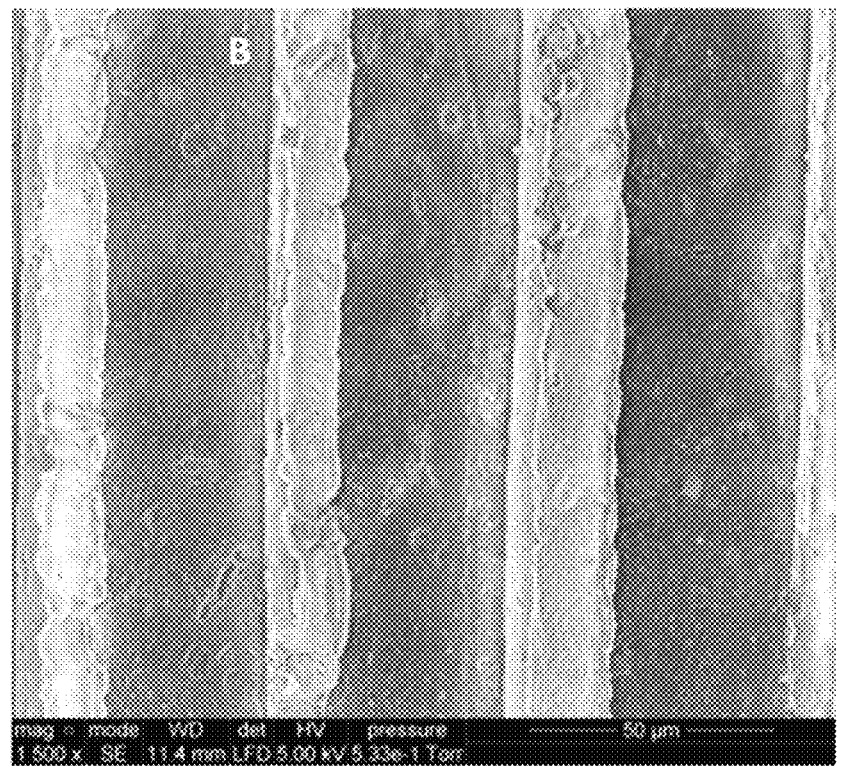

SEM images of shadow mask-patterned PCLF tubes in FIG. 8 show stripes of $ZrO_2$-SAMP throughout the surface.

The shadow masking method successfully patterned thin PCLF tubes, showing that shadow mask patterning of the inside of tubes is scalable to various dimensions including those required for clinical testing of nerve conduits. Suitable neurons and neural cells for such nerve conduits include neurons from CNS or PNS, neural support cells such as Schwann cells and radial glial cells, neural stem cells such as cells that form neurospheres, and neural tumor cells such as glioblastoma and neuroblastoma cells.

Thus, a flat KAPTON® mask could be manipulated to pattern curved or tube-shaped PCLF surfaces. This represents the first method developed to pattern curved surfaces and the inside of tubes using a CVD procedure, which has implications for research on patterning surfaces that are not compatible with standard methods of microfabrication, and which are useful within the realm of tissue scaffolding as well as in other areas.

Example 9. Construction of Shadow Masks for Small Polymer Tubes

Figure 9:
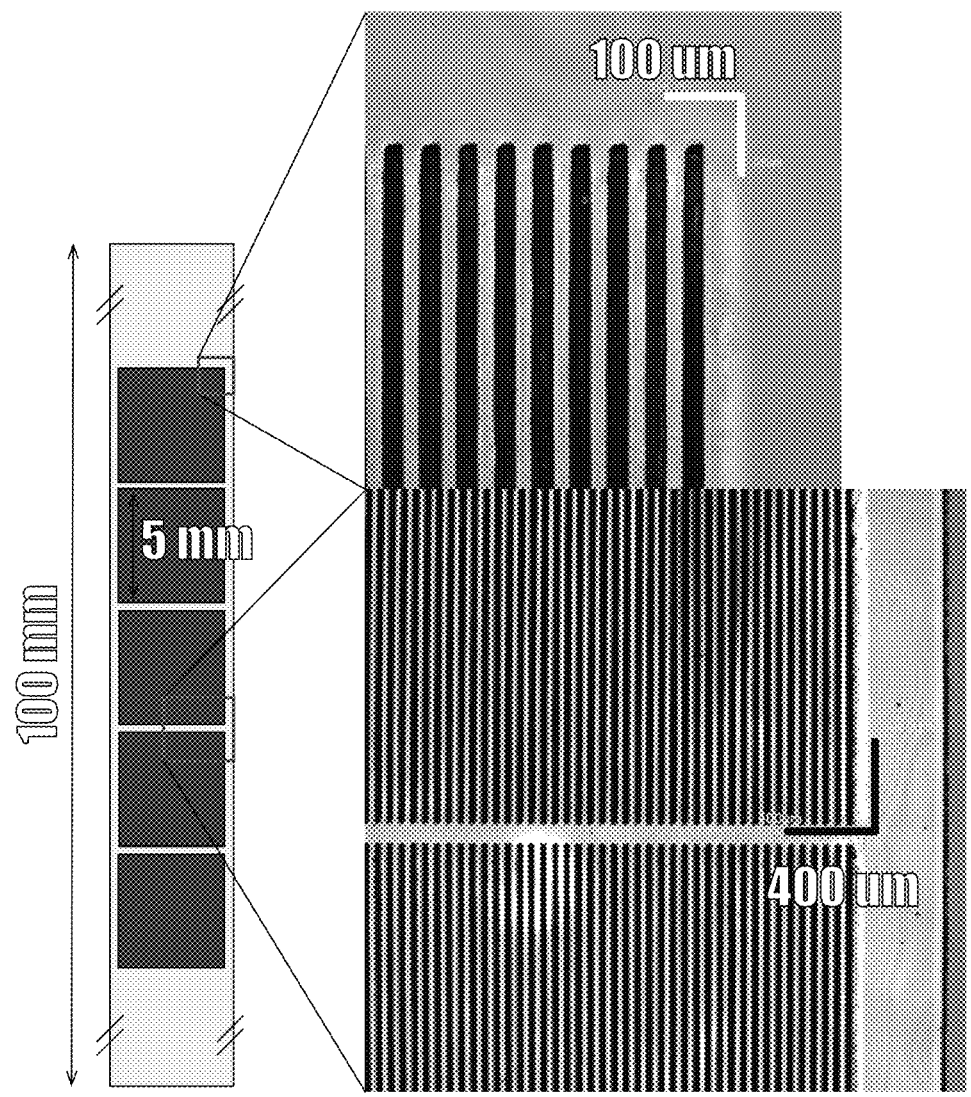
FIG. 9 shows a schematic diagram of a typical shadow mask for patterning the inside of small tubes, and SEM pictures of sections of a typical mask.
Figures 10A, 10B:
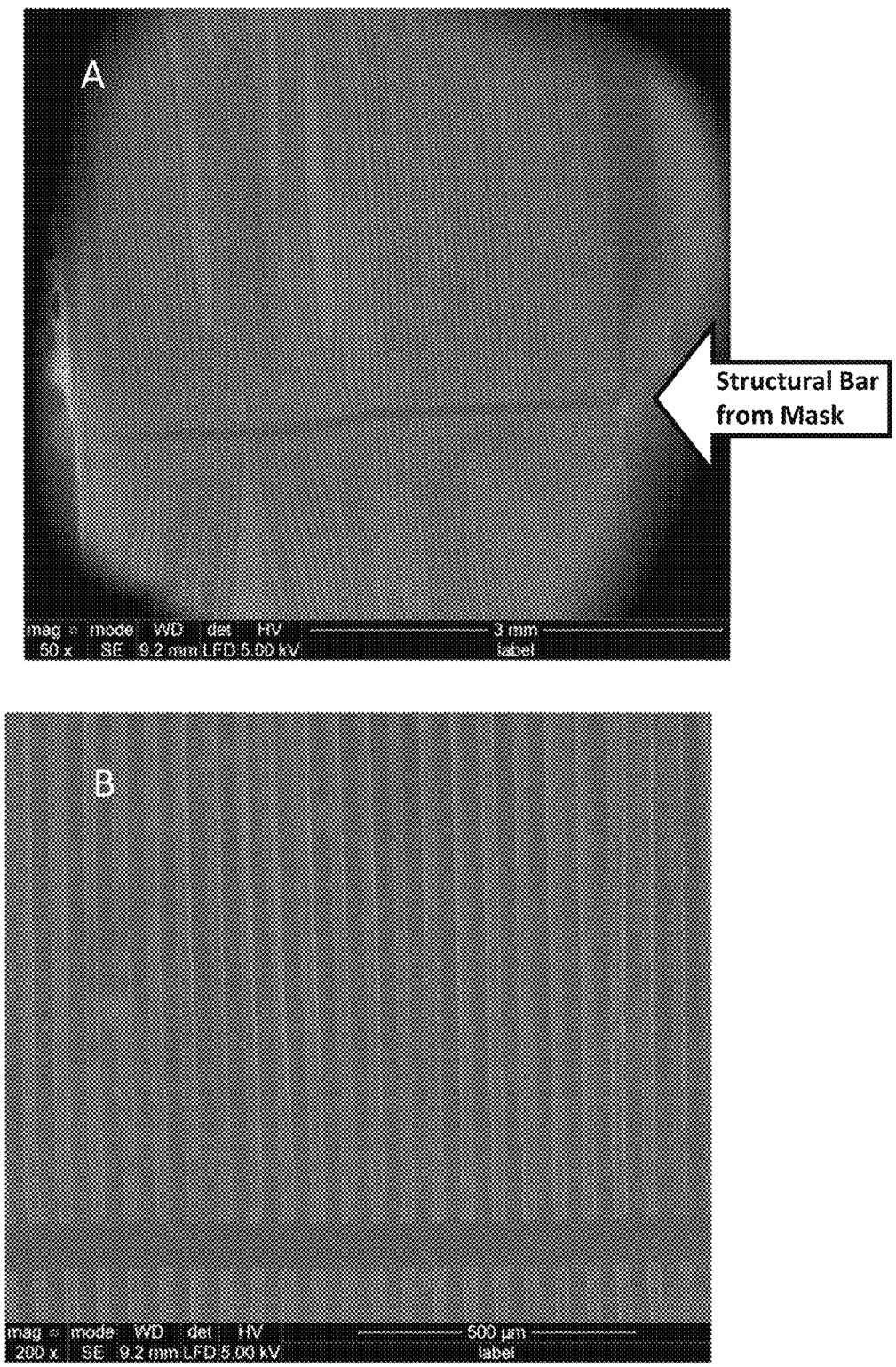
FIGS. 10A and 10B.
Figure 11A:
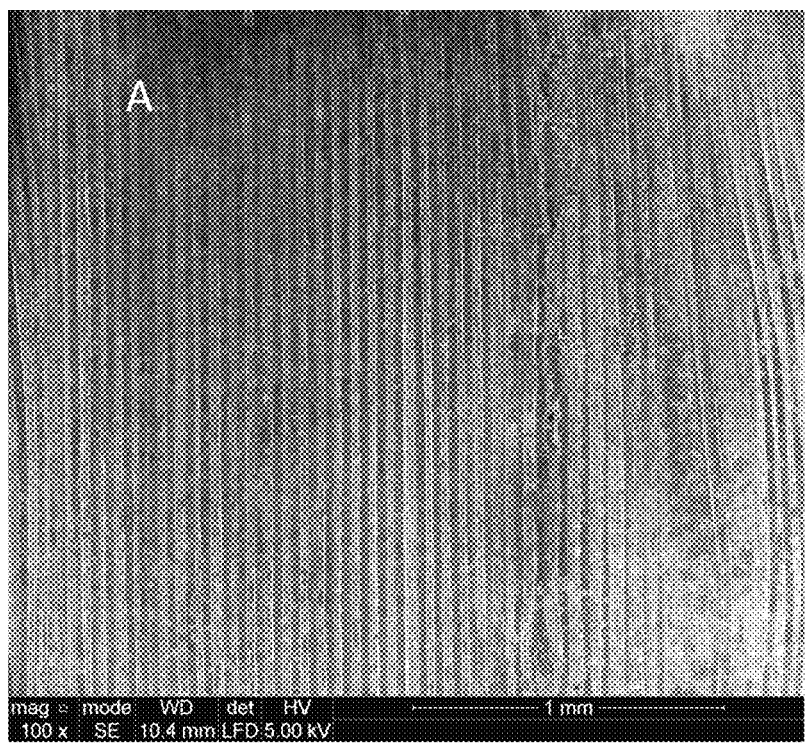
FIGS. 11A and 11B.
Figure 11B:
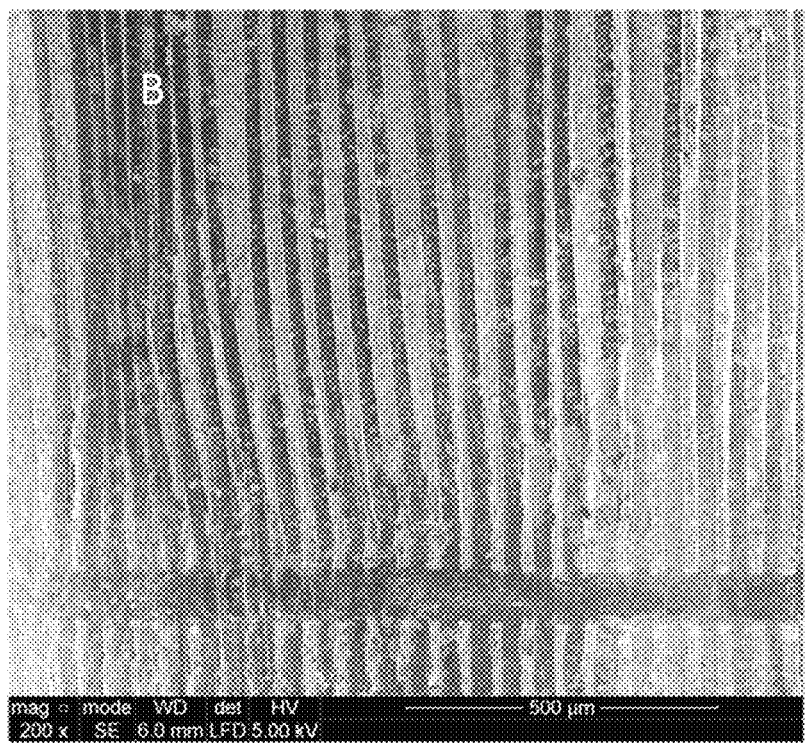
Figure 12A:
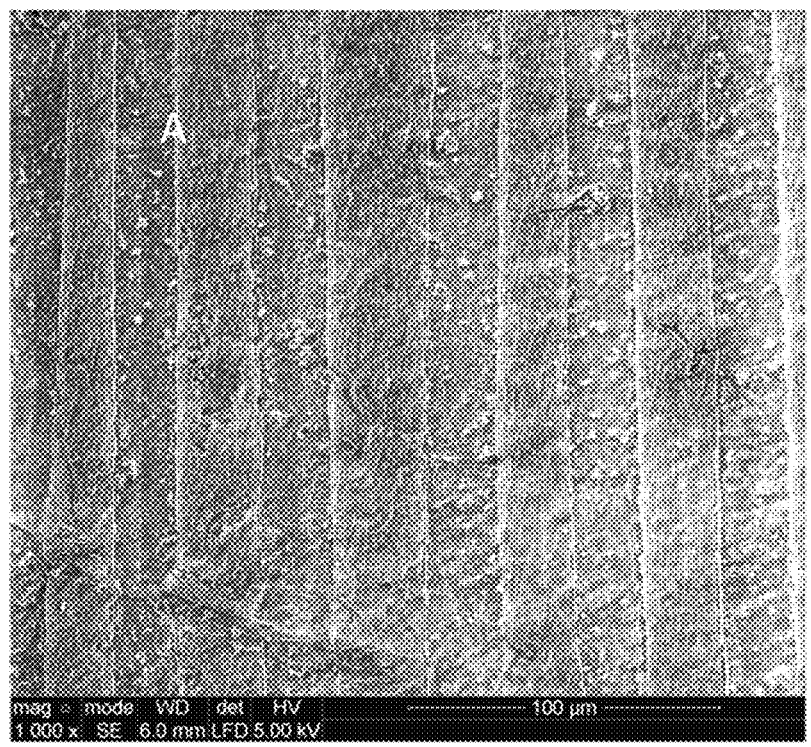
FIGS. 12A and 12B.
Figure 12B:
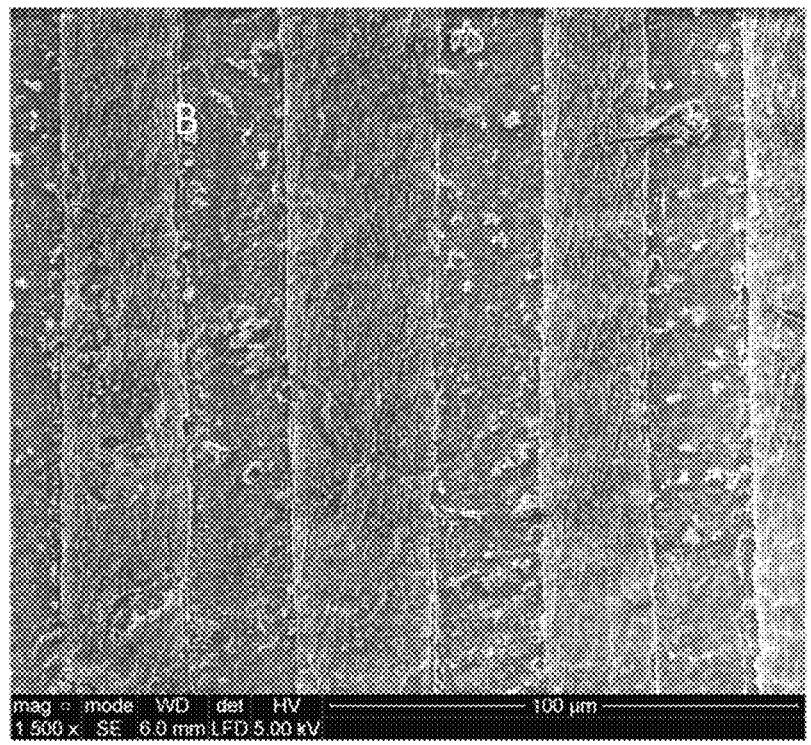
Figure 13:
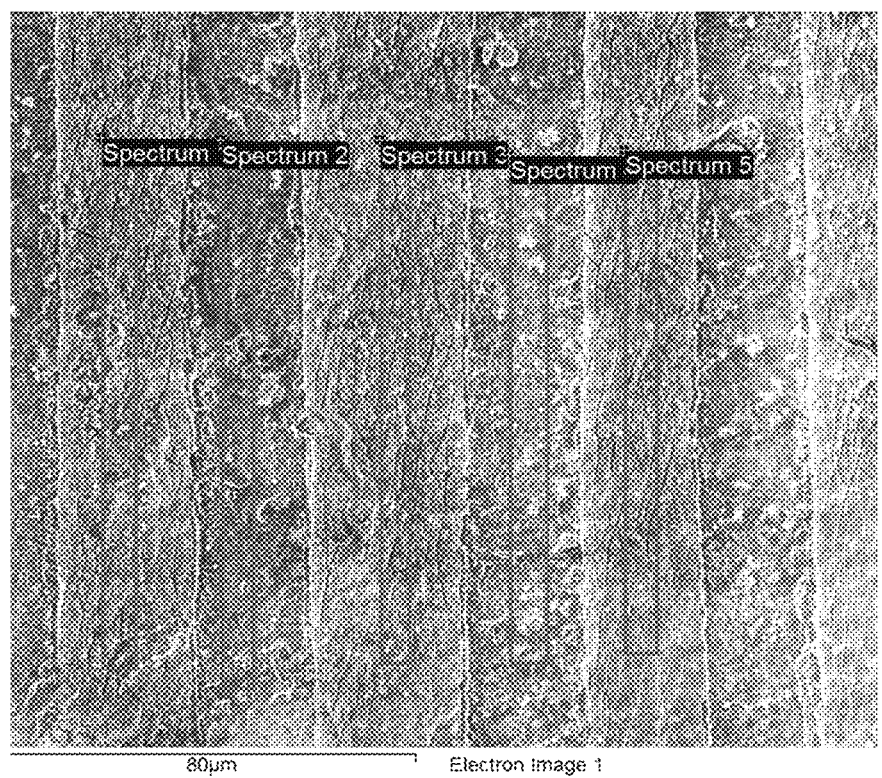
Figure 14A:
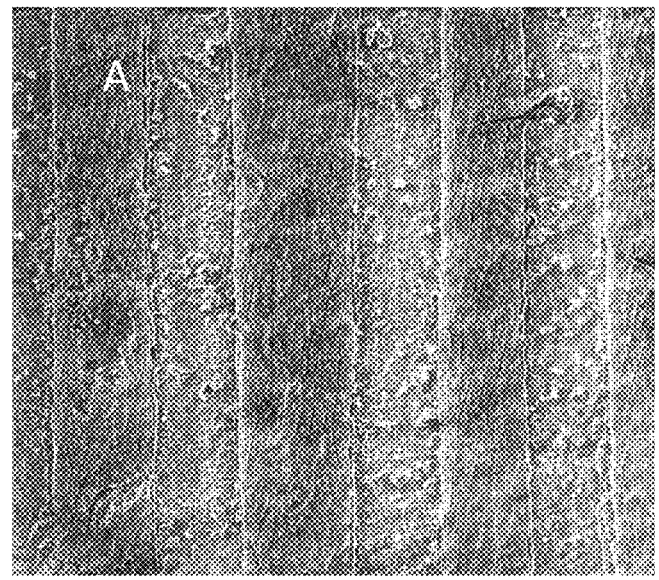
FIGS. 14A and 14B.
Figure 14B:
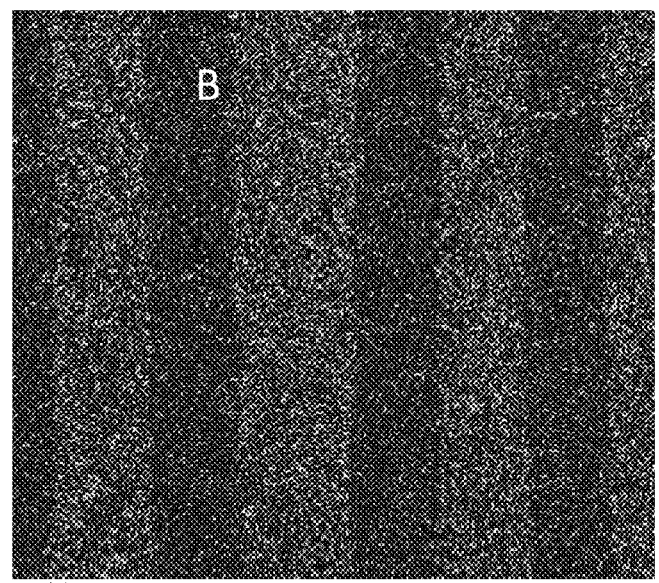
Figure 15:
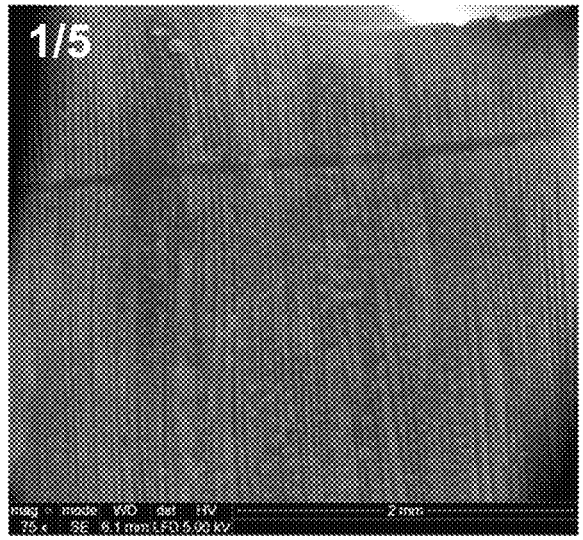
Figure 15:
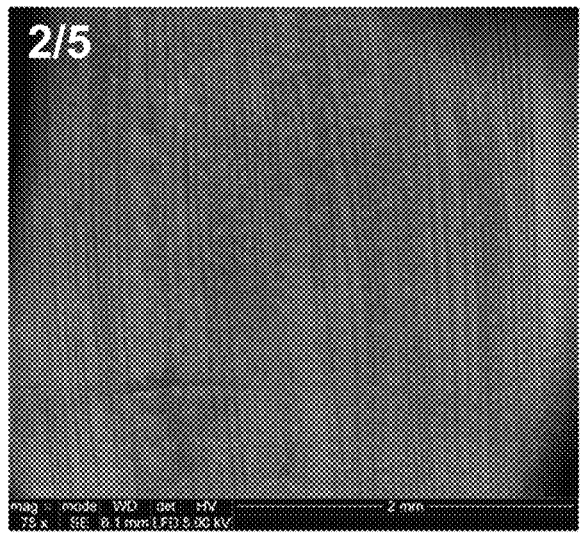
Figure 15:
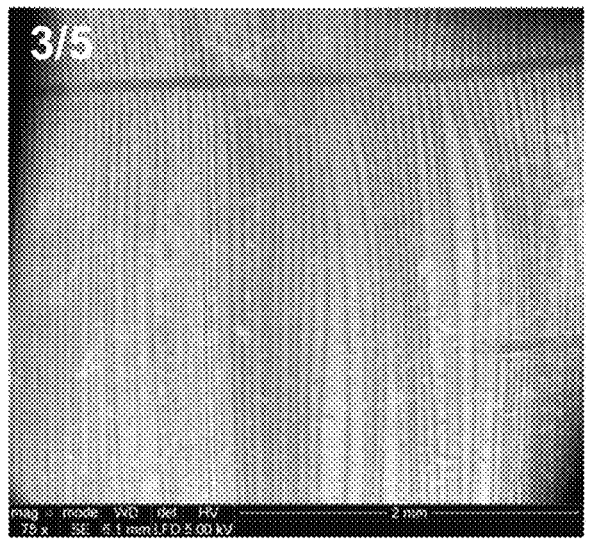
Figure 16:
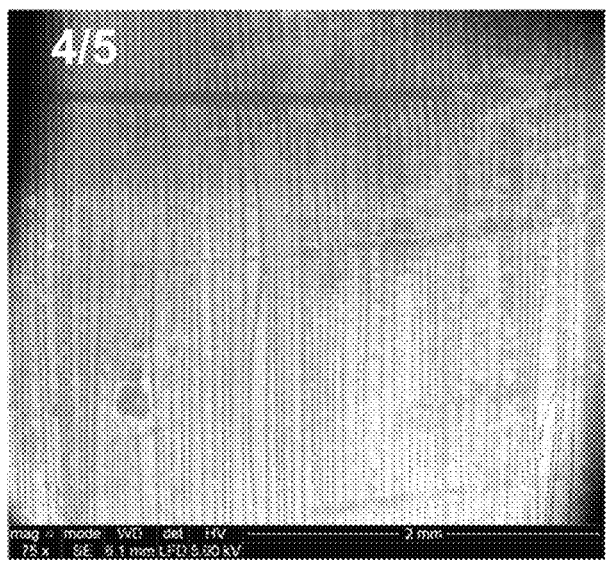
Figure 16:
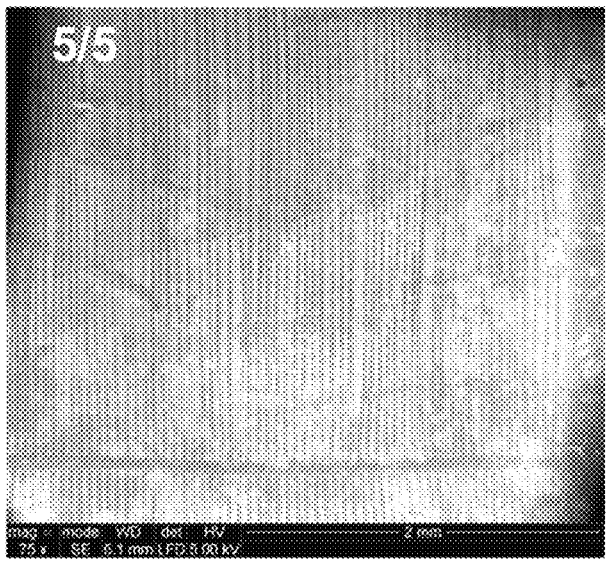
Figure 17A:
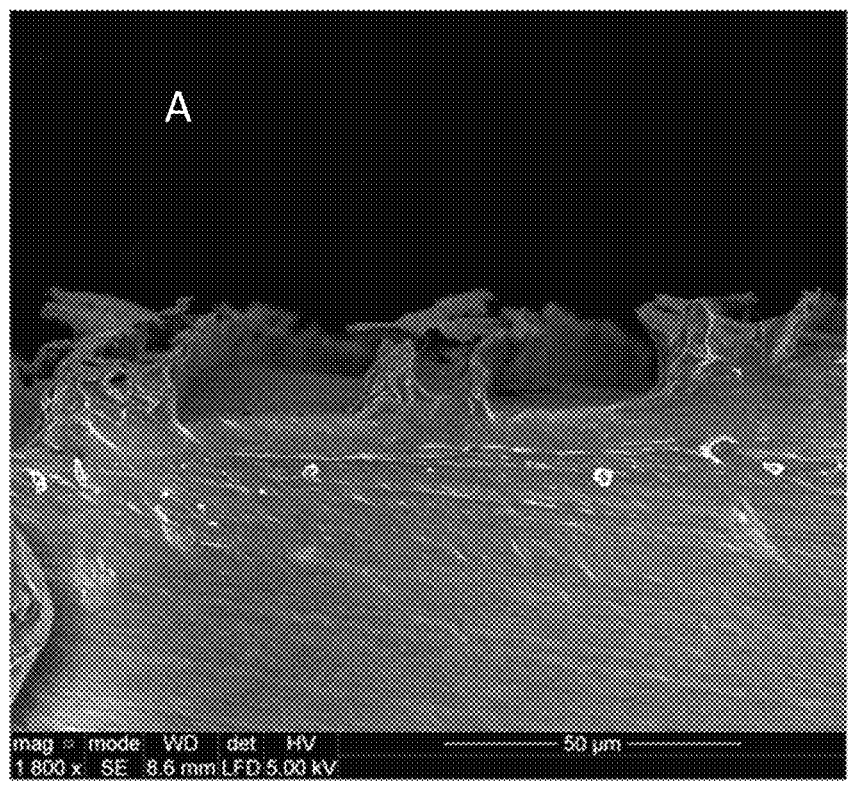
FIGS. 17A and 17B show cross-sectional SEM images of a physically patterned 1.5 mm ID PCLF tube demonstrating that applying pressure to the shadow mask while heating creates a physical pattern in the polymer. 17A and 17B show the same tube cross section at different magnifications. Channel depth is about 4-5 μm.
Figure 17B:
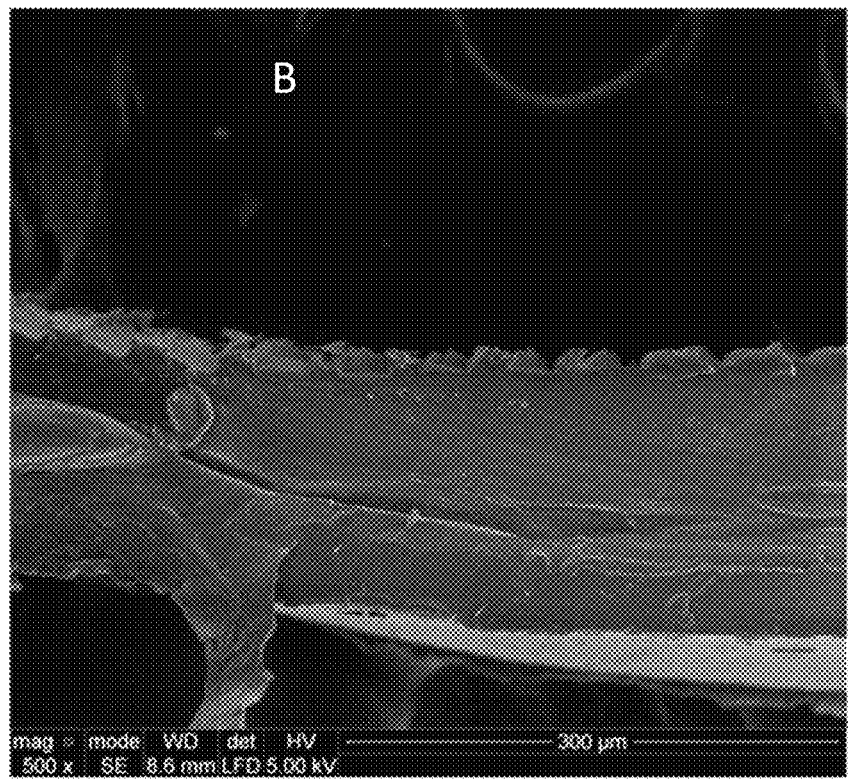

Shadow masks for use in small tubes (1.5 mm ID or less) were designed to maintain a mechanical integrity over long length scales with patterning on small length scales. The mask was machined by laser or otherwise to create 30 micrometer by 50,000 micrometer (5 cm) openings in a 5 mm by 100 mm strip. The mask is made of sections or segments where the 30 micrometer openings are extended to 5,000 micrometers long, after which the pattern is disrupted by a cross support (structural bar) of the shadow mask polymer in order to maintain the mechanical integrity of the shadow mask. The shadow mask is made of sufficiently thin polymeric material to allow for easily deforming the mask to cover conformal to the inside of a cylindrical sample (i.e., a tube to be patterned). For KAPTON® polyimide masks, the thickness of the mask polymer ranges from about 10 µm to about 120 µm, preferably from about 10 to about 75 µm, more preferably from about 20 to about 50 µm. Thicker masks do not readily conform to the inside diameter of small (e.g. 1 mm ID) tubes, and the thinner masks tend to be fragile in handling, so the choice of thickness depends on the physical properties of the mask polymer as well as on the inside diameter of the tube substrate. A typical shadow mask is shown in FIG. 9.

The laser used for machining the mask was a pulsed diode pumped solid state (neodymium-doped yttrium orthovanadate) laser, with a frequency tripled output operating wavelength of 355 nanometers. The laser energy was roughly 30 microJoules per pulse, and operated up to 25 kilohertz. The laser was focused to a spot size of approximately 10 micrometers in diameter. High precision linear translation stages were used to position the sample and trigger the laser to fire at every 0.5 micrometer of motion, to produce a 10 micrometer wide cut having the desired pattern in the mask.

Example 10. Embossed (Physically Patterned) Polymer for Alignment of Cells

PCLF polymer tubes internally embossed with a physical pattern as above were submerged and incubated with soluble rat fibronectin (10 µg/ml) in phosphate buffered saline (PBS) for 1 hour at 37° C. The tubes were then washed 3 times with PBS and 40,000 cells/cm$^2$ were seeded onto the polymer. The cell-seeded polymer tubes were cultured for 1 day or 7 days. Phase contrast images of the polymer and patterned lines are shown in FIG. 18A.

After 1 day or 7 days, polymer tubes bearing attached cells were fixed in 3.7% formaldehyde solution for 20 minutes and were immunostained for actin. 1-Day and 7-day images (FIG. 18A) show that cells attach and align themselves across the surface-embossed substrate and grow to confluency while maintaining alignment.

Figures 18A, 18B:
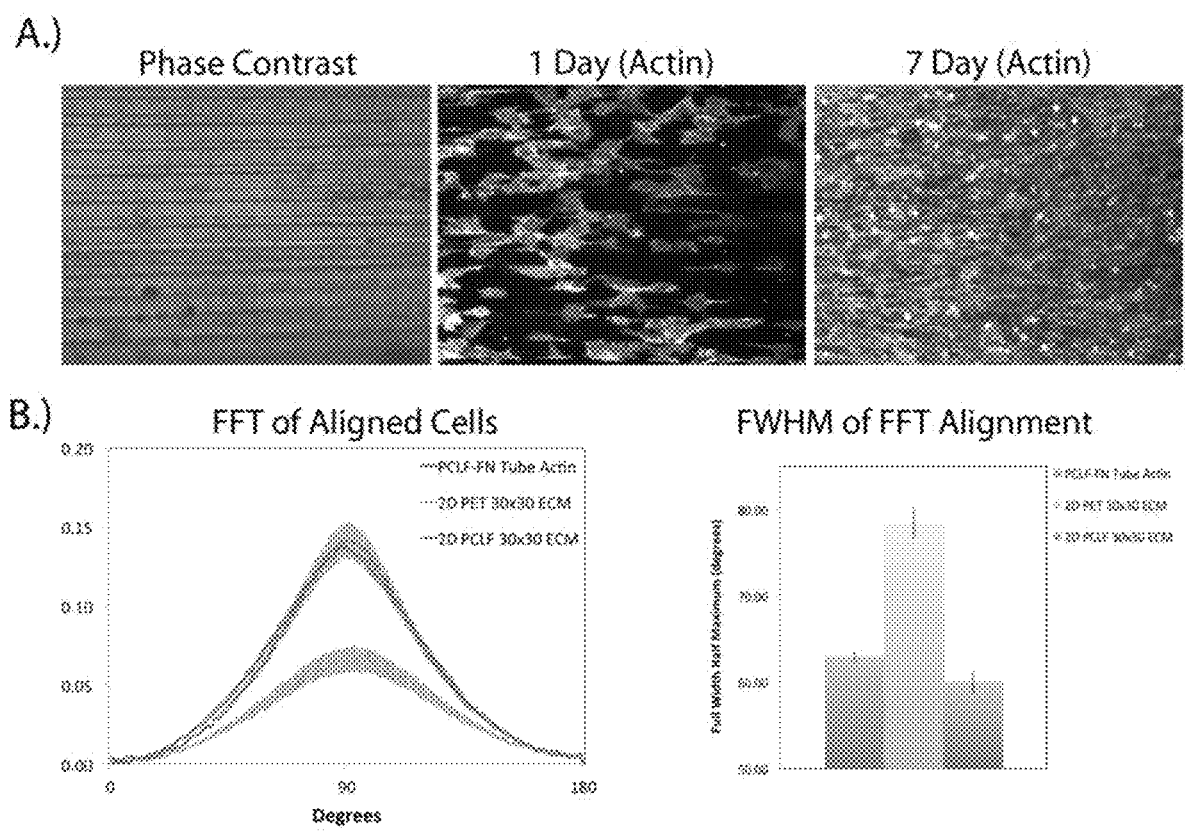
FIGS. 18A and 18B shows a comparison of the alignment of surface-embossed PCLF polymer tubes incubated with cells attached by fibronectin, versus polymers having aligned ECM using Zr(O-tBu)$_4$/SAMP (Self-Assembled Monolayer of Phosphonate) attachment.

Fast Fourier Transform (FFT) analysis was performed on the actin-stained images to determine alignment of cells on shadow mask patterned polymers, FIG. 18B. Extracellular matrix (ECM) alignment for the surface-embossed PCLF tubes treated with fibronectin was compared to alignment on a coupon of PCLF patterned with ZrO$_2$-SAMP and a coupon of poly(ethylene terephalate) (PET) patterned with ZrO$_2$-SAMP. Full width half max (FWHM) of FFT graphs were used to compare alignments using the ZrO$_2$-SAMP surface chemistry and shadow mask tube patterning-fibronectin approaches as shown in FIG. 18B. These data show that cells align on the fibronectin-treated embossed surface as well as they do on ZrO$_2$-SAMP patterned PCLF and better than on patterned PET.

Example 11. Embossing OPF Using a Shadow Mask

Figure 20A:
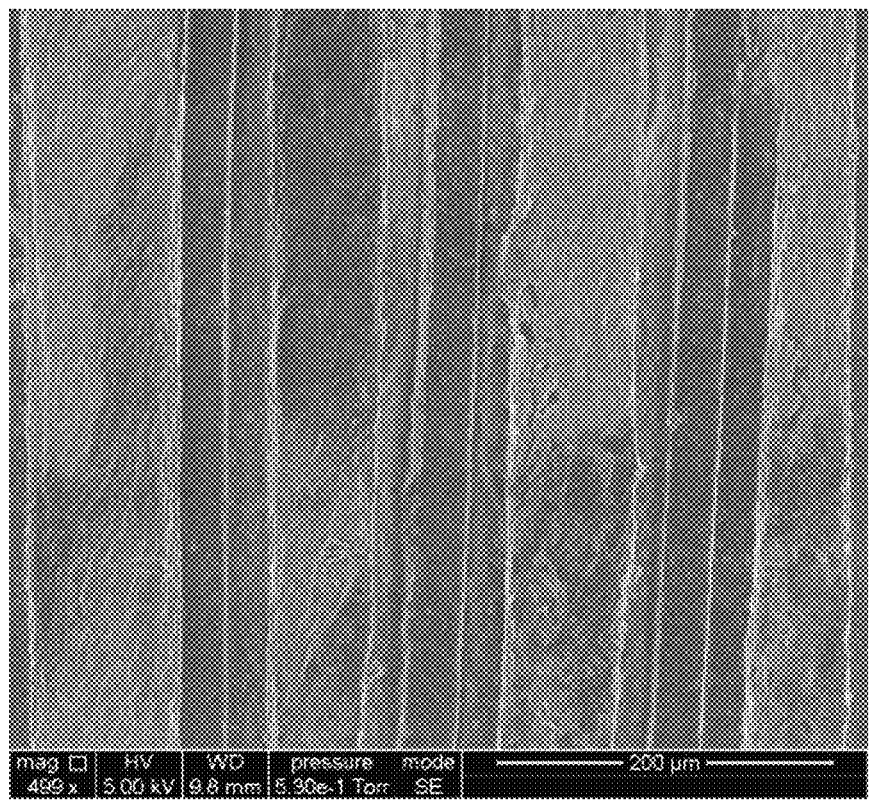
FIGS. 20A and 20B shows the results of surface treatment of OPF with shadow masking: An SEM image of embossed OPF with Zr/SAMP treatment (20A) and its cross section (20B); areas covered by the mask are shown as darker indentations, whereas the areas not covered by the mask are bright, high ridges.
Figure 20B:
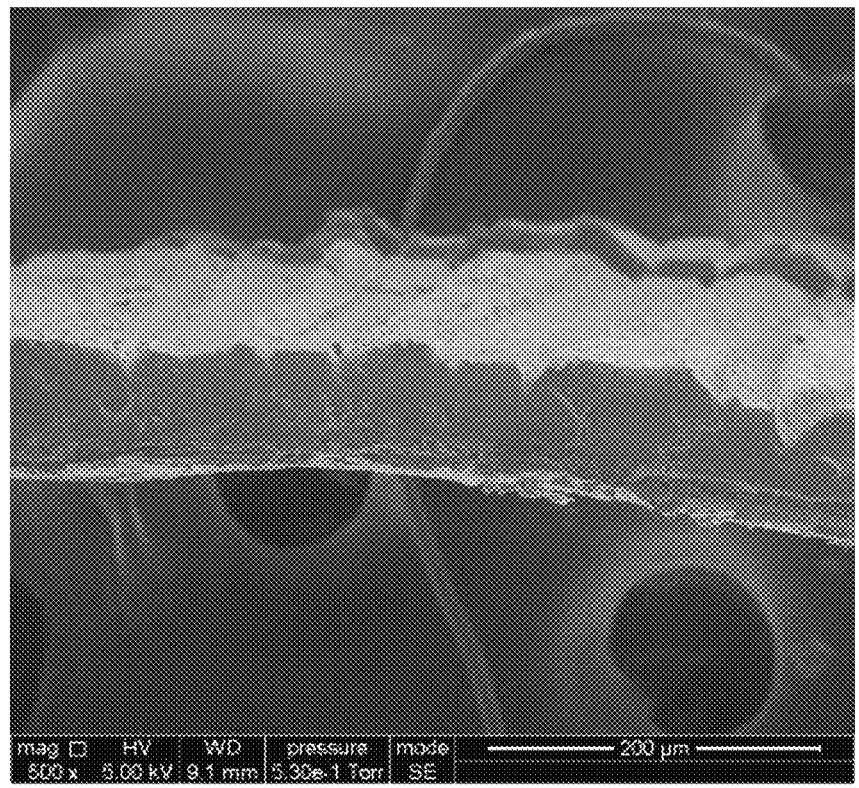

OPF is a soft and flexible polymer that has a T$_g$ of about 55° C. Since the primary form of OPF is a hydrogel, the material presents itself as a polymeric matrix that easily swells up to about 800% of its original weight in water. When a dry piece of OPF was heated to its T$_g$, the polymer softens can be shaped with some slight pressure. Exploiting this malleable characteristic of OPF, a piece of OPF (FIG. 19A) was patterned by embossing a 30 µm-lined shadow mask onto its surface, as shown in FIG. 19B. Since OPF was designed as a biomedical hydrogel that can be used for drug delivery, the hydrogel is essentially porous. Therefore, with some pressure, the piece of polymer was compressed, giving not only surface embossment but also a change in its cross section, as shown in FIG. 19C. This method of patterning the piece of polymer proved to maintain the surface's chemical integrity (FIG. 19). An infrared (IR) analysis showed that the chemical composition on the OPF surface before and after patterning remained the same. Aside from physically changing the topography of the OPF surface to form physical ridges, shadow masking can also be used as a physical blockage when an interface is deposited onto the polymer surface, leaving behind surface treatments only on exposed areas. When a shadow mask was left on the OPF surface while the material underwent chemical vapor deposition (CVD) with vapor of zirconium tetra(tert-butoxide) and then treated with a phosphonic acid solution, a layer of Zr/SAMP adhered to the exposed OPF surface while the areas covered by shadow masking remained clear (FIG. 20). To discern between the Zr/SAMP distribution on shadow-masked OPF, with the limitations introduced by the X-Ray beam size, both an EDS element mapping and a line scan provided a more accurate analysis of where in the pattern the elements were restricted. The results of element mapping and line scanning on the OPF EDS indicated that most Zr and P atoms were confined to the bright stripes as shown in the electron images captured by the SEM.

Example 12. Embossing TECOFLEX™ Using a Shadow Mask

Figure 22A:
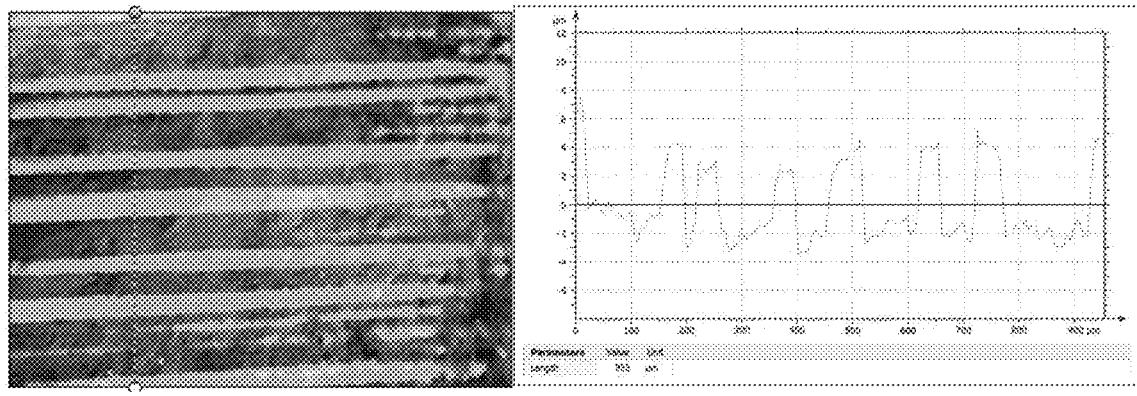
FIGS. 22A and 22B show a profile of embossed TECOFLEX™ EG-80A from 3D confocal microscopy: (22A) embossed TECOFLEX™ with large ridges, up to 6 μm in height; (22B) embossed TECOFLEX™ with small ridges, as low as 2 μm.
Figure 22B:
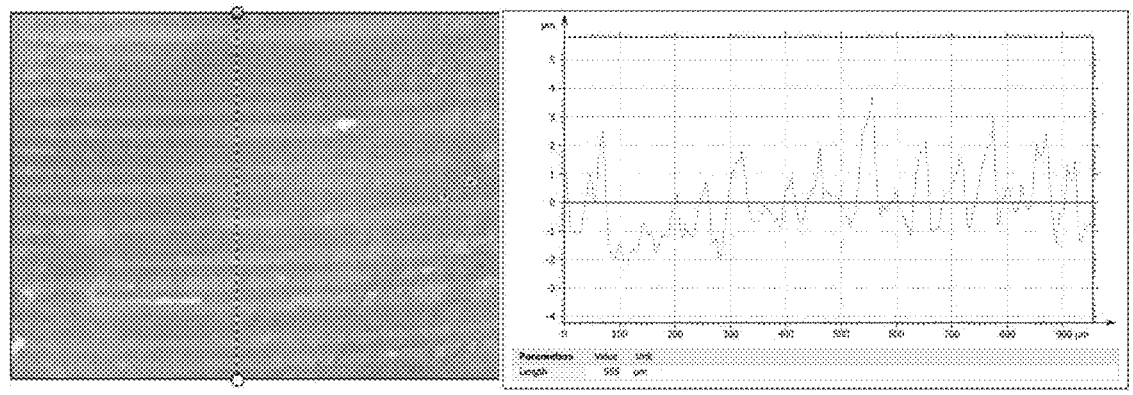
Figure 23A:
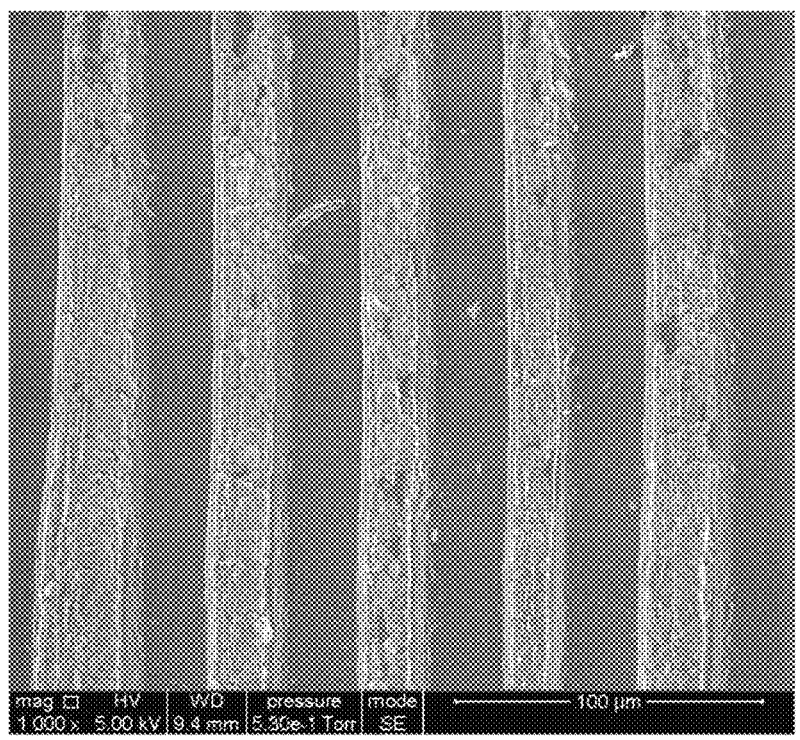
FIGS. 23A and 23B show the results of surface treatment of TECOFLEX™ with shadow masking: An SEM image of embossed TECOFLEX™ with Zr/SAMP treatment (23A)
Figure 23B:
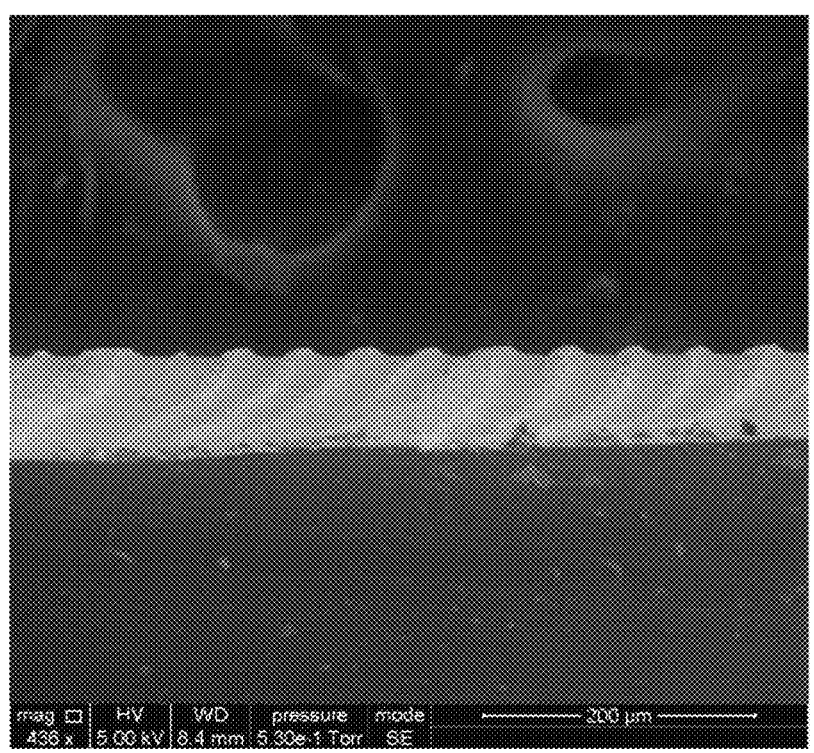

TECOFLEX™ is a flexible, medical-grade aliphatic polyether-based thermoplastic polyurethane. The T$_g$ of TECOFLEX™ EG-80A, the softest grade of clear TECOFLEX™ (supplied by Lubrizol) was found to be about 80° C. At this temperature, the material is sticky and can easily be adhered to a KAPTON® mask, similar to that of dehydrated OPF. However, unlike dehydrated OPF, this material is elastic and slightly stretchable, even at room temperature, so its elasticity enables it to bounce back to its original shape and provides a lower degree of physical modification (embossing). However, FIGS. 21 and 22 show that this polymer also provides a useful substrate for embossing. As for OPF, the process of shadow masking preserves the chemical integrity of the TECOFLEX™ surface. An IR analysis before and after embossing did not show much spectral differences, with all the distinctive peaks still in place.

The shadow mask was concluded to have intimate adherence to the surface because subsequent Zr/SAMP surface treatment showed distinct differences on the surface. Qualitatively, the surface appeared cloudy with the interface and upon analysis under ESEM and EDS, the Zr/SAMP interface was found only on areas not covered by the shadow mask, leaving unexposed areas with little Zr and P detected. Some cracking on Zr/SAMP stripes were observed because the polymer swelled when it was being put into a phosphonic acid solution for SAMP treatment. However, upon drying, the polymer shrank to its original size with no major pattern modifications. To discern between the Zr/SAMP distribution on shadow-masked TECOFLEX™ due to limitations of the X-Ray beam size, both an EDS element mapping and a line scan proved to be more telling in terms of where the elements were restricted. As noted above for OPF, both the P and Zr atoms were largely confined to the bright stripes on the electron images captured by the SEM, showing that the shadow mask successfully blocks the deposition of these elements on the sample surface.

Thus, shadow masking has now been demonstrated to be a technique that acts as a template to physically pattern the surfaces of soft and flexible polymers, such as PCLF, dehydrated OPF and TECOFLEX™ EG-80A. Physically, shadow masking under appropriate temperature and pressure conditions modifies the surface topography of these materials. Porous and compressible dehydrated OPF conformed to the shape of the masks, resulting in ridged patterns. However, the elastic TECOFLEX™ was more resistant to physical change. Regardless, both materials managed to adhere intimately with the KAPTON® shadow masks when they were heated to their $T_g$. Upon their adherence, during surface treatments, shadow masks acted as physical barriers to block the growth of a chemical interface on these surfaces. As a result, a patterned Zr/SAMP interface was successfully deposited on both dehydrated OPF and TECOFLEX™ via shadow masking. Thus, a flexible KAPTON® shadow mask can pattern soft, flexible materials such as the aforementioned polymers, which cannot be achieved by traditional surface patterning via photolithography.

Other Embodiments

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the present claims.

All publications cited herein are incorporated by reference in their entirety for all purposes.

What is claimed is:

1. A polymeric substrate, wherein at least a portion of said substrate comprises a fragile material or a material from which photoresist developed on the surface thereof cannot be removed without impairing the intended purpose of said substrate, said material comprising raised surfaces in the form of a pattern that is configured to attach tissue cells and direct their growth in alignment.

2. The polymeric substrate of claim 1, wherein the raised pattern comprises the polymer of said polymeric substrate.

3. The polymeric substrate of claim 1, wherein the raised pattern is coated with at least one cell-binding or cell-adhesive material.

4. The polymeric substrate of claim 3, wherein said cell-binding or cell-adhesive material comprises fibronectin.

5. The polymeric substrate of claim 1, further comprising curvature.

6. The polymeric substrate of claim 5, wherein said substrate comprises a curved surface selected from the group consisting of inward-curving concave surfaces and outward-curving convex surfaces.

7. The polymeric substrate of claim 1, wherein the polymeric substrate is in the form of a tube or a rolled structure and the raised-patterned surface is on the interior of the tube or rolled structure.

8. A method of patterning a surface of a polymeric substrate which is fragile or is a material from which photoresist developed on the surface thereof cannot be removed without impairing the intended purpose of said substrate, comprising the steps of
    a) providing a shadow mask comprising a plurality of openings defining a pattern,
    b) contacting the shadow mask with a surface of said polymeric substrate to form a masked substrate,
    c) applying pressure to the shadow mask surface of the masked substrate under conditions effective to emboss the substrate surface with the pattern defined by said mask, and
    d) removing the mask to reveal a patterned polymeric surface.

9. The method of claim 8, wherein said pressure is applied to said masked substrate with heating sufficient to form a phase transition in the polymer of said substrate, followed by cooling said masked substrate.

10. The method of claim 8, wherein said substrate surface geometry incompatibility further comprises surface curvature.

11. The method of claim 10, where the patterning is on the inside surface of a tube, a rolled substrate, or a folded substrate.

12. The method of claim 8, wherein said polymeric substrate is a preformed tube and said patterning is on the inside surface of the tube.

13. A construct which supports cell attachment and alignment, comprising:
    a) a polymeric substrate of claim 1, wherein at least a portion of a surface of said substrate comprises a fragile material or a material from which photoresist developed on the surface thereof cannot be removed without impairing the intended purpose of said substrate, in a pattern that is raised above the surface of said substrate; and
    b1) a patterned coating of a metal alkoxide, oxide or mixed oxide-alkoxide disposed thereon; and a phosphonic acid covalently attached to said metal alkoxide patterned coating, which phosphonic acid comprises at least one cell-binding functional group; or
    b2) a cell-adhesive biomaterial disposed thereon;
wherein said pattern is configured to attach tissue cells and direct their growth in alignment.

14. The construct of claim 13, further comprising cells attached thereto.

15. The construct of claim 13, further comprising an aligned extracellular matrix (ECM).

16. The construct of claim 13, wherein said substrate further comprises surface curvature.

17. The construct of claim 13, wherein said phosphonic acid comprises one or more functional groups selected from the group consisting of polyol moieties, sugar alcohol moieties, hydroxyl functional groups, amino functional groups, carboxylic acid functional groups, carboxylate ester functional groups, phosphonic acid functional groups, phosphonate functional groups, ether functional groups, alkyne functional groups, azide functional groups and thiol functional groups.

18. The construct of claim 17, wherein said phosphonic acid is 1,4-butanediphosphonic acid.

19. The construct of claim 13, wherein said substrate comprises a polymer selected from the group consisting of polyamides, polyureas, polyesters, polyketones, polyimides, polysulfides, polysulfoxides, polysulfones, polythiophenes, polypyridines, polypyrroles, polyethers, silicone (polysiloxanes), polysaccharides, fluoro-polymers, epoxies, aramides, amides, imides, polypeptides, polyolefins, polyethylene, polystyrene, poly-propylene, liquid crystal polymers, thermoplastics, polyvinyls, poly(vinyl alcohol), polyacrylics, polyacrylates, poly(acrylic acid), polycarbonates, polytetrafluoroethylene (PTFE), polyethylene terephthalate (PET), poly(vinyl-pyrrolidone), poly(2-hydroxyethyl methacrylate), poly(N-vinylpyrrolidone), poly(methyl methacrylate), polyethylene-co-vinyl acetate), poly(methacrylic acid), polylactides (PLA), polyglycolides (PGA), poly(lactide-co-glycolides) (PLGA), polylactones, polyanhydrides, polyphosphazenes, polyorthoesters, polycaprolactone fumarate (PCLF), oligo-(polyethylene glycol) fumarate (OPF), PEDOT:PSS, poly(ethylene oxide), poly(ethylene glycol), cross-linked poly(acrylic acid), poly(acrylamides), aliphatic polyether-based thermoplastic polyurethanes, sucrose, carbohydrate glass, silk, collagen, alginate, chitosan, and chondroitin, copolymers and derivatives thereof, and composites including these polymers.

20. The construct of claim 19, wherein said substrate polymer comprises PCLF, OPF, or an aliphatic polyether-based thermoplastic polyurethane.

21. The construct of claim 13, where said patterned coating is on the inside surface of a tube, a rolled substrate, or a folded substrate.

22. The construct of claim 13, wherein said phosphonic acid has the formula (I)

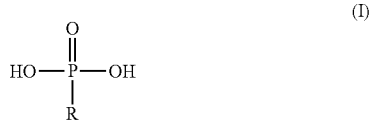

wherein R is an alkylene group omega-substituted with another phosphonic acid functional group to form an α,ω-diphosphonic acid.

23. A method of preparing a construct which supports cell attachment and alignment, said method comprising:
a) providing a substrate formed from a fragile material or a material from which photoresist developed on the surface thereof cannot be removed without impairing the intended purpose of said substrate;
b) preparing a shadow mask template consisting of a material which is adherent to said substrate such that the peel strength therebetween is less than the tensile strength of either of said shadow mask or the substrate material; and
c) adhering said shadow mask template to said substrate to form a substrate-mask ensemble, wherein said shadow mask comprises a pattern of openings that expose portions of said substrate.

24. The method of claim 23, further comprising:
d) exposing said substrate-mask ensemble to a metal alkoxide to form a treated substrate-mask ensemble;
e) warming the treated ensemble to bond said metal alkoxide to said exposed portions of said substrate and removing said mask from said treated substrate-mask ensemble to provide a metal oxide and alkoxide pattern bonded to said substrate surface; and
f) covalently attaching to said metal oxide and alkoxide pattern a phosphonic acid comprising at least one cell-binding functional group.

25. The method of claim 23, further comprising:
d) exposing said substrate-mask ensemble to a cell-adhesive biomaterial to form a treated substrate-mask ensemble; and
e) removing said mask from said treated substrate-mask ensemble to form a cell-adhesive pattern on said substrate surface.

26. The method of claim 25, wherein said cell-adhesive biomaterial comprises fibronectin.

27. The method of claim 24, further comprising:
attaching cells to said construct.

28. The method of claim 24, further comprising:
incubating said construct to form an aligned extracellular matrix (ECM).

29. The method of claim 23, wherein said substrate is nonplanar.

30. The method of claim 29, wherein said nonplanar surface comprises surface curvature.

31. The method of claim 30, wherein said substrate comprises tube, a rolled structure, or a folded structure, wherein the inside surface of the substrate is patterned.

32. The method of claim 24, wherein said phosphonic acid comprises one or more functional groups selected from the group consisting of polyol moieties, sugar alcohol moieties, hydroxyl functional groups, amino functional groups, carboxylic acid functional groups, carboxylate ester functional groups, phosphonic acid functional groups, phosphonate functional groups, ether functional groups, alkyne functional groups, azide functional groups and thiol functional groups.

33. The method of claim 32, wherein said phosphonic acid is 1,4-butanediphosphonic acid.

34. The method of claim 23, wherein said substrate comprises a polymer selected from the group consisting of polyamides, polyureas, polyesters, polyketones, polyimides, polysulfides, polysulfoxides, polysulfones, polythiophenes, polypyridines, polypyrroles, polyethers, silicone (polysiloxanes), polysaccharides, fluoro-polymers, epoxies, aramides, amides, imides, polypeptides, polyolefins, polyethylene, polystyrene, poly-propylene, liquid crystal polymers, thermoplastics, polyvinyls, poly(vinyl alcohol), polyacrylics, polyacrylates, poly(acrylic acid), polycarbonates, polytetrafluoroethylene (PTFE), polyethylene terephthalate (PET), poly(vinyl-pyrrolidone), poly(2-hydroxyethyl methacrylate), poly(N-vinylpyrrolidone), poly(methyl methacrylate), polyethylene-co-vinyl acetate), poly(methacrylic acid), polylactides (PLA), polyglycolides (PGA), poly(lactide-co-glycolides) (PLGA), polylactones, polyanhydrides, polyphosphazenes, polyorthoesters, polycaprolactone fumarate (PCLF), oligo-(polyethylene glycol) fumarate (OPF), PEDOT:PSS, poly(ethylene oxide), poly(ethylene glycol), cross-linked poly(acrylic acid), poly(acrylamides), aliphatic polyether-based thermoplastic polyurethanes, sucrose, carbohydrate glass, silk, collagen, alginate, chitosan, and chondroitin, copolymers and derivatives thereof, and composites including these polymers.

35. The method of claim 34, wherein said substrate polymer comprises PCLF, OPF or an aliphatic polyether-based thermoplastic polyurethane.

36. The method of claim 35, wherein said substrate polymer is PCLF.

37. The method of claim 35, wherein said substrate polymer is an aliphatic polyether-based thermoplastic polyurethane.

* * * * *

UNITED STATES PATENT AND TRADEMARK OFFICE
CERTIFICATE OF CORRECTION

PATENT NO. : 10,646,896 B2
APPLICATION NO. : 15/649033
DATED : May 12, 2020
INVENTOR(S) : Jeffrey Schwartz et al.

It is certified that error appears in the above-identified patent and that said Letters Patent is hereby corrected as shown below:

On the Title Page

Item [72] should read:
Jeffrey Schwartz, Princeton, NJ (US);
Stephen Bandini, Newton, MA (US);
Lily Adler, New York, NY (US);
Alomi Parikh, Seattle, WA (US);
Richard Lu, Ballwin, MO (US);
Audrey Meng, San Francisco, CA (US);
Kelly Lim, Melaka (MY);
Romain Fardel, New York, NY (US);
Joshua Spechler, Cherry Hill, NJ (US);
Craig Arnold, Princeton, NJ (US);
Jean Schwarzbauer, Princeton, NJ (US)

Signed and Sealed this
Twenty-first Day of February, 2023

Katherine Kelly Vidal
*Director of the United States Patent and Trademark Office*